(12) United States Patent
Thubrikar et al.

(10) Patent No.: US 11,357,628 B2
(45) Date of Patent: Jun. 14, 2022

(54) APPARATUS AND METHOD FOR DELIVERY OF A PROSTHETIC VALVE DEVICE

(71) Applicant: THUBRIKAR AORTIC VALVE, INC., Norristown, PA (US)

(72) Inventors: Mano J. Thubrikar, Schwenksville, PA (US); Samuel B. Evans, Blue Bell, PA (US)

(73) Assignee: THUBRIKAR AORTIC VALVE, INC.

( * ) Notice: Subject to any disclaimer, the term of this patent is extended or adjusted under 35 U.S.C. 154(b) by 0 days.

(21) Appl. No.: 17/265,377

(22) PCT Filed: Jul. 24, 2019

(86) PCT No.: PCT/US2019/043226
§ 371 (c)(1),
(2) Date: Feb. 2, 2021

(87) PCT Pub. No.: WO2020/033146
PCT Pub. Date: Feb. 13, 2020

(65) Prior Publication Data
US 2021/0244538 A1 Aug. 12, 2021

Related U.S. Application Data

(60) Provisional application No. 62/714,832, filed on Aug. 6, 2018.

(51) Int. Cl.
*A61F 2/24* (2006.01)
*A61F 2/95* (2013.01)

(52) U.S. Cl.
CPC .......... *A61F 2/2436* (2013.01); *A61F 2/2427* (2013.01); *A61F 2/95* (2013.01); *A61F 2/9517* (2020.05)

(58) Field of Classification Search
CPC .... A61F 2/2436; A61F 2/2427; A61F 2/9517; A61F 2/95; A61F 2/24; A61F 2/06;
(Continued)

(56) References Cited

U.S. PATENT DOCUMENTS

| 5,797,952 A | 8/1998 | Klein |
| 8,137,398 B2 | 3/2012 | Tuval et al. |

(Continued)

FOREIGN PATENT DOCUMENTS

| CA | 2944307 | 6/2003 | |
| WO | WO-2013118362 A1 * | 8/2013 | ............. A61F 2/962 |

OTHER PUBLICATIONS

European Supplementary Search Report issued in European Patent Application No. EP19846040 dated Aug. 16, 2021, pp. 1-8.

*Primary Examiner* — Kelly J Bekker
*Assistant Examiner* — Andrew P. Restaino
(74) *Attorney, Agent, or Firm* — The Belles Group, P.C.

(57) ABSTRACT

A catheter and a method for using the catheter to implant a replacement aortic valve into a patient. The catheter includes an expandable wall, an outer sheath, a first tube operably coupled to the expandable wall, and a second tube operably coupled to the expandable wall. The catheter also includes a pusher that is fixed to the second tube, the pusher being spaced apart from the expandable wall by a distance that is sufficient to accommodate the replacement aortic valve. The outer sheath is movable relative to the expandable wall so that in one state the expandable wall is disposed within the outer sheath and in another state the expandable wall is located outside of the outer sheath. The expandable wall is configured to radially expand. The catheter also includes a handle assembly that is adjusted by a surgeon to achieve the functions of the catheter.

17 Claims, 29 Drawing Sheets

(58) Field of Classification Search
CPC .... A61F 2/01; A61F 2/962; A61F 2/07; A61F 2/958; A61F 2/844; A61F 2/915; A61F 2/966; A61F 2/9661; A61F 2/9662; A61F 2002/9665; A61M 29/00
See application file for complete search history.

(56) References Cited

U.S. PATENT DOCUMENTS

| | | | |
|---|---|---|---|
| 8,403,976 B2* | 3/2013 | Sachar | A61F 2/958 623/1.11 |
| 8,470,023 B2 | 6/2013 | Eidenschink et al. | |
| 8,480,725 B2 | 7/2013 | Rasmussen et al. | |
| 8,663,318 B2 | 3/2014 | Ho | |
| 9,023,095 B2 | 5/2015 | Bueche et al. | |
| 9,173,760 B2 | 11/2015 | Belhe et al. | |
| 9,585,748 B2 | 3/2017 | Wright | |
| 9,855,128 B2 | 1/2018 | Kolbel et al. | |
| 2007/0227544 A1 | 10/2007 | Swann et al. | |
| 2007/0282436 A1 | 12/2007 | Pinchuk | |
| 2009/0216310 A1 | 8/2009 | Straubinger et al. | |
| 2010/0234940 A1 | 9/2010 | Dolan | |
| 2011/0046726 A1 | 2/2011 | Delgado | |
| 2011/0077731 A1* | 3/2011 | Lee | A61F 2/958 623/1.11 |
| 2011/0264201 A1 | 10/2011 | Yeung et al. | |
| 2012/0101571 A1 | 4/2012 | Thambar | |
| 2012/0179244 A1 | 7/2012 | Schankereli et al. | |
| 2013/0282113 A1* | 10/2013 | Punga | A61F 2/2418 623/2.17 |
| 2015/0127092 A1* | 5/2015 | Straubinger | A61F 2/2436 623/2.11 |
| 2015/0164667 A1 | 6/2015 | Vinluan et al. | |
| 2016/0030171 A1 | 2/2016 | Quijano et al. | |
| 2016/0287386 A1 | 10/2016 | Alon et al. | |
| 2019/0151086 A1* | 5/2019 | Lally | A61B 17/1204 |

* cited by examiner

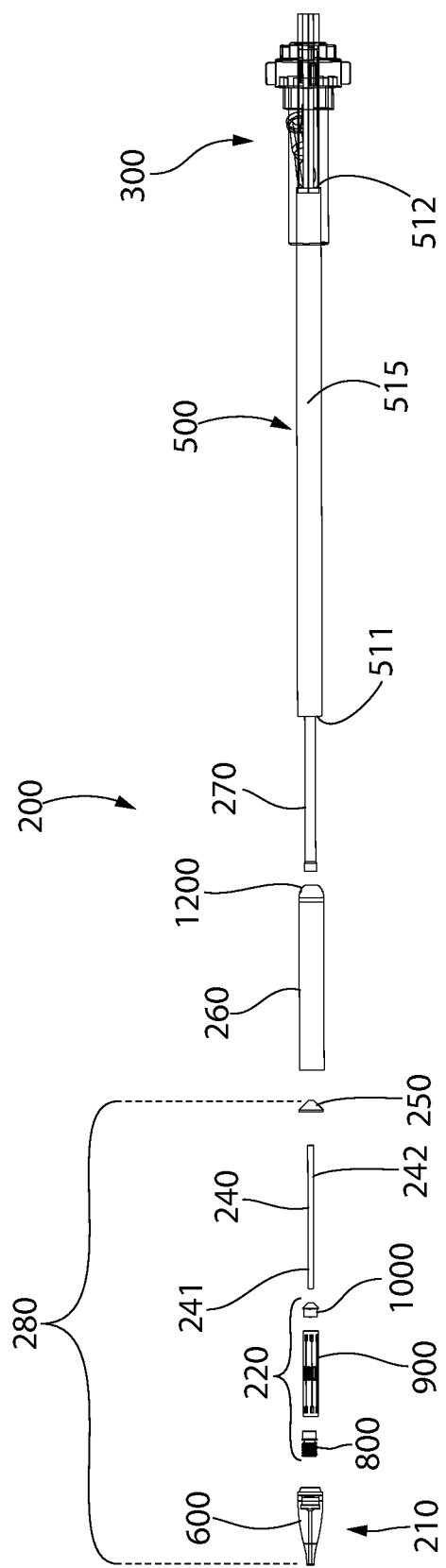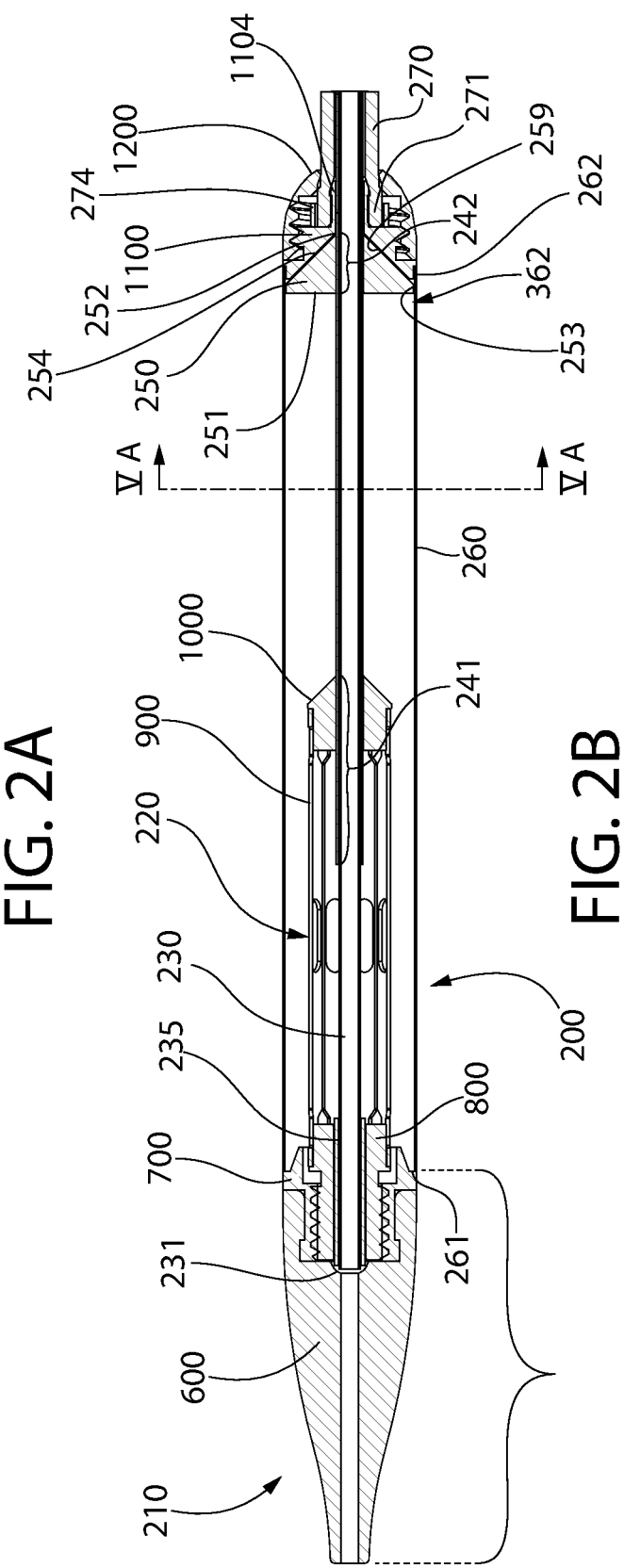

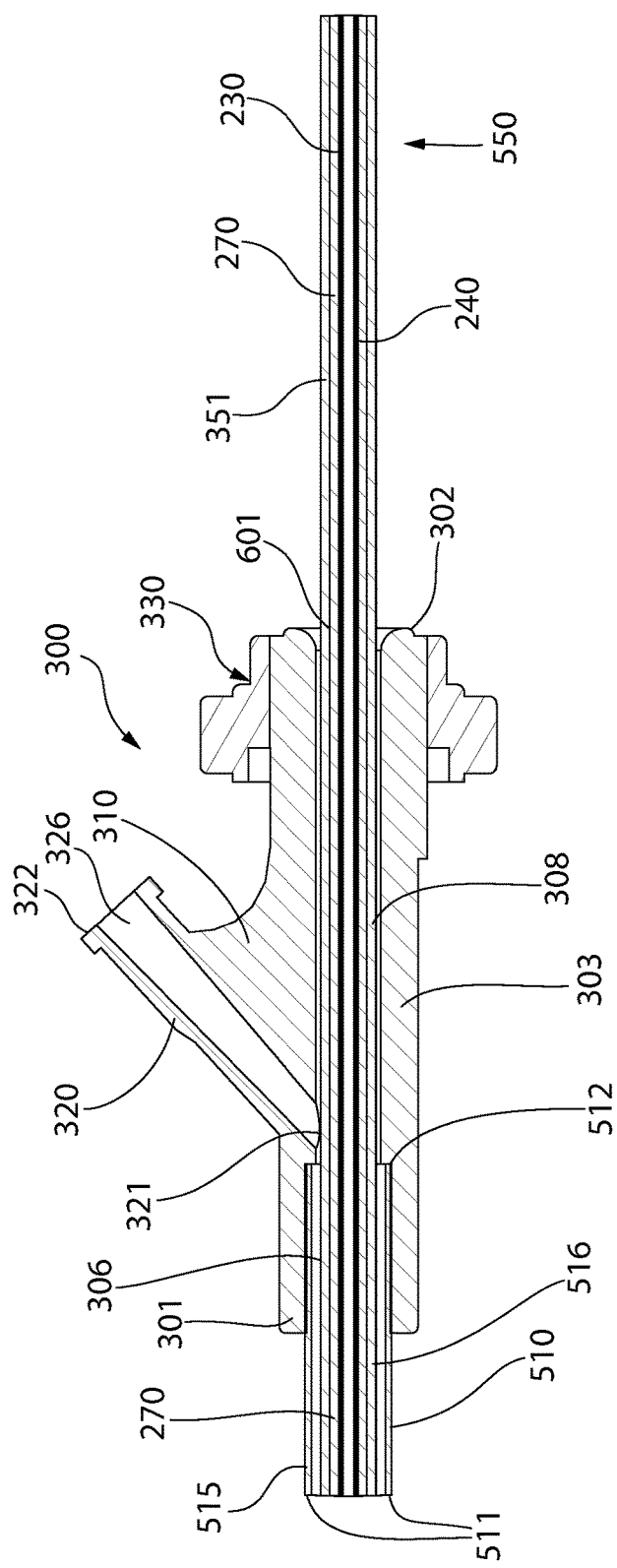
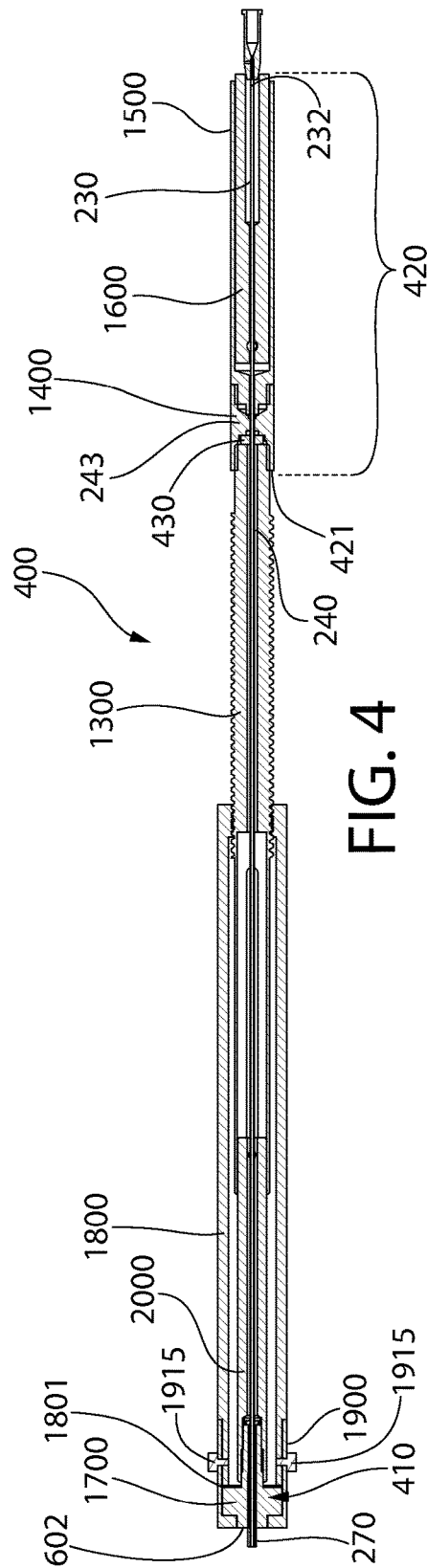
FIG. 3
FIG. 4

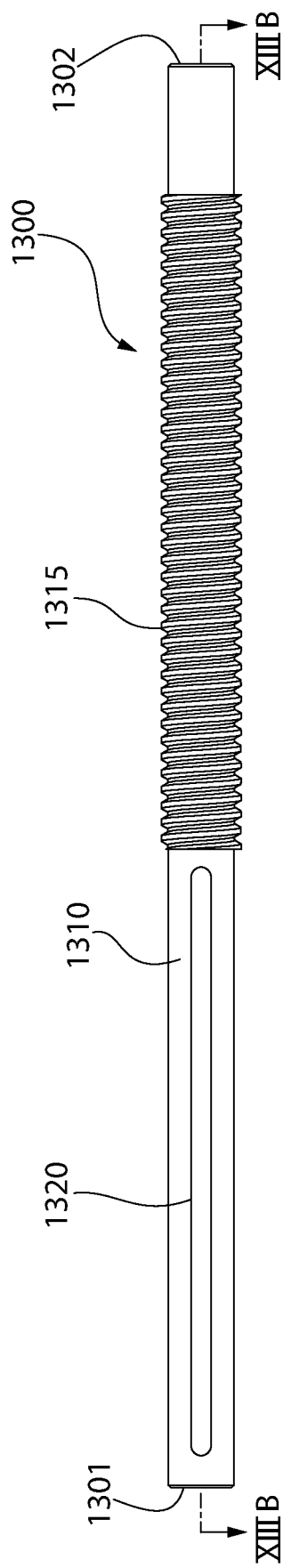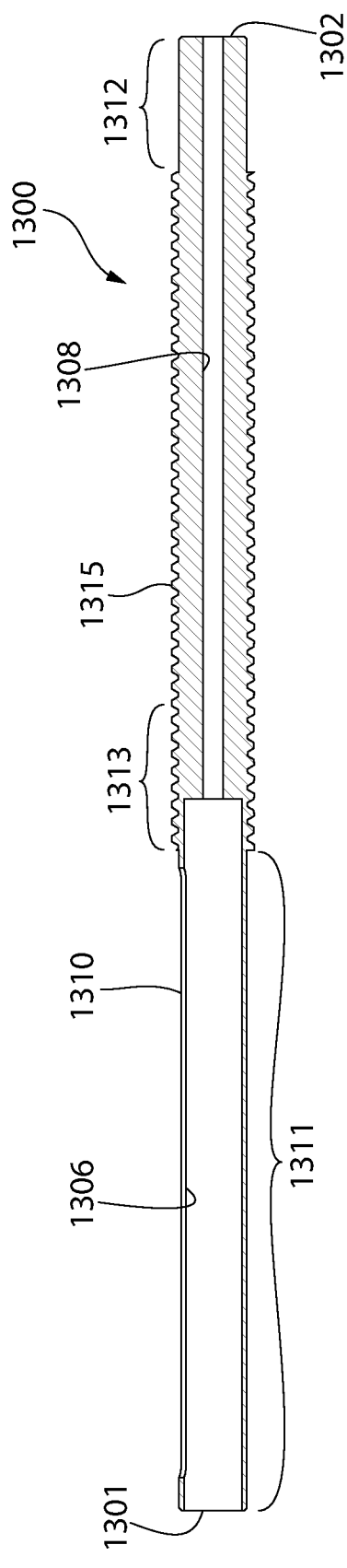
FIG. 13A
FIG. 13B

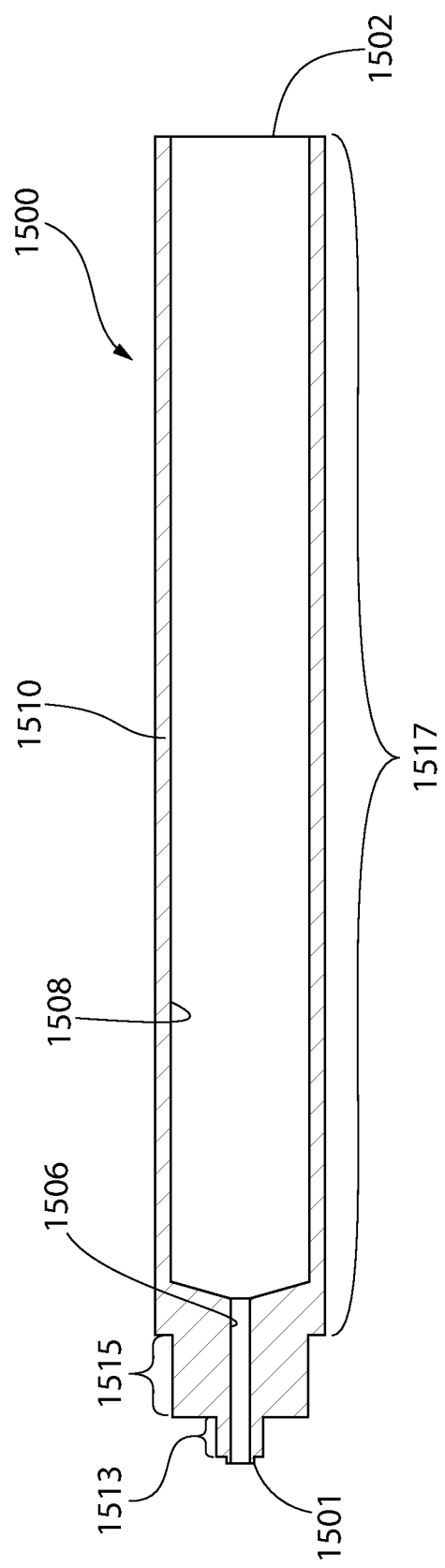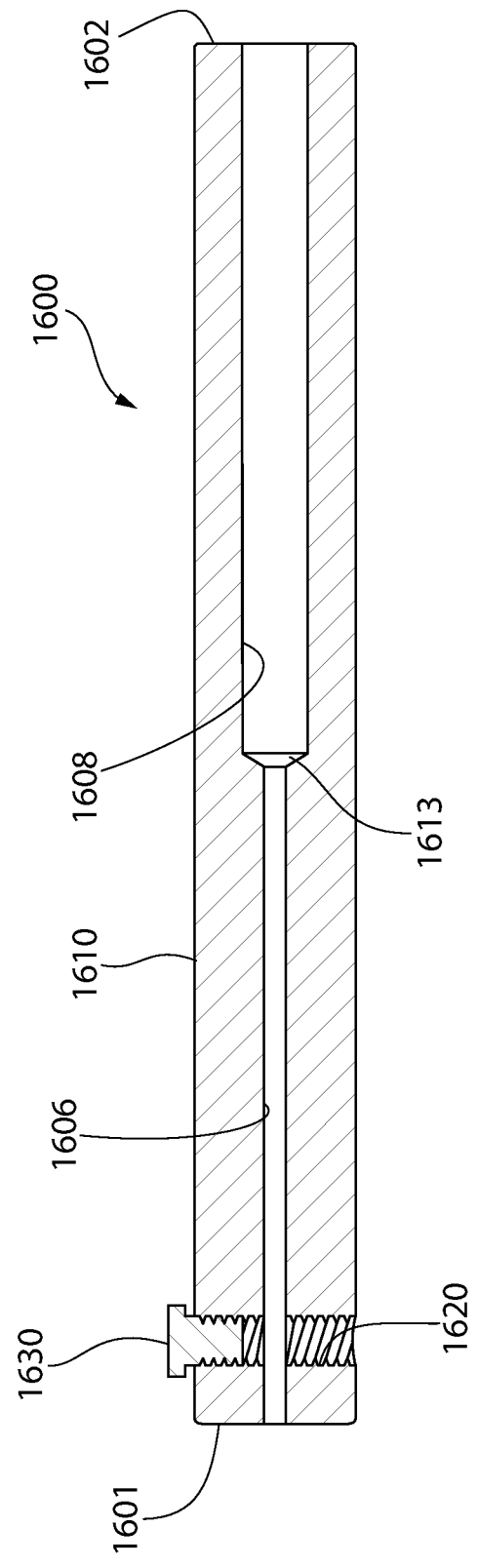
FIG. 15B
FIG. 16

APPARATUS AND METHOD FOR DELIVERY OF A PROSTHETIC VALVE DEVICE

CROSS-REFERENCE TO RELATED APPLICATIONS

The present application is a national phase entry under 35 U.S.C. § 371 of PCT/US2019/043226, filed Jul. 24, 2019, which claims priority to U.S. Provisional Patent Application Ser. No. 62/714,832, filed Aug. 6, 2018, the entireties of which are incorporated herein by reference.

BACKGROUND

Heart valve disease continues to be a significant cause of morbidity and mortality. Heart valve replacement has become a routine surgical procedure for patients suffering from valve regurgitation or stenotic calcification of the leaflets. Until recently, the vast majority of heart valve replacements entailed a full sternotomy and placing the patient on cardiopulmonary bypass. Traditional open surgery inflicts significant patient trauma and discomfort, requires extensive recuperation times and may result in life-threatening complications. To address these concerns, within the last fifteen years efforts have been made to perform cardiac valve replacements using minimally-invasive techniques, such as a percutaneous entry with a transluminal delivery. These surgical techniques, generally referred to as Transcatheter Aortic Valve Implantations (TAVI) or Transcatheter Aortic Valve Replacements (TAVR), use a catheter to deliver a prosthetic valve device to an implantation site using a patient's lumen of the vascular system.

SUMMARY

The present invention is directed to a catheter and a method for using the catheter to implant a replacement aortic valve into a patient. The catheter includes an expandable wall, an outer sheath, a first tube operably coupled to the expandable wall, and a second tube operably coupled to the expandable wall. The catheter also includes a pusher that is fixed to the second tube, the pusher being spaced apart from the expandable wall by a distance that is sufficient to accommodate the replacement aortic valve. The outer sheath is movable relative to the expandable wall so that in one state the expandable wall is disposed within the outer sheath and in another state the expandable wall is located outside of the outer sheath. The expandable wall is configured to radially expand. The catheter also includes a handle assembly that is adjusted by a surgeon to achieve the functions of the catheter.

In one aspect, the invention may be a catheter comprising: an expandable wall assembly comprising a distal end and a proximal end; a first tube operably coupled to the distal end of the expandable wall assembly; a second tube operably coupled to the proximal end of the expandable wall assembly, at least a portion of the first tube being disposed within at least a portion of the second tube; a pusher attached to the second tube, the pusher spaced from the expandable wall assembly by a distance sized to accommodate a replacement aortic valve; an outer sheath having a lumen; and wherein the outer sheath is movable between: (1) a first position wherein an expandable wall of the expandable wall assembly is located within the lumen of the outer sheath; and (2) a second position wherein the expandable wall of the expandable wall assembly is not located within the lumen of the outer sheath.

In another aspect, the invention may be a catheter comprising: an expandable wall assembly comprising a distal end and a proximal end; a first tube coupled to the distal end of the expandable wall assembly; a second tube coupled to the proximal end of the expandable wall assembly; a pusher attached to the second tube in an axially spaced apart manner from the expandable wall assembly; a replacement aortic valve disposed around the second tube between the expandable wall assembly and the pusher; an outer sheath defining a lumen, at least a portion of the expandable wall assembly, the pusher, the replacement aortic valve, the first tube, and the second tube located within the lumen of the outer sheath; and wherein the outer sheath is slidable relative to the expandable wall assembly, the pusher, the replacement aortic valve, the first tube, and the second tube.

In yet another aspect, the invention may be a method for implanting a replacement aortic valve, the method comprising: inserting a distal end of a catheter into a vasculature of a patient until a replacement aortic valve retained by the catheter is positioned at a desired location, the catheter including an outer sheath having a lumen within which the replacement aortic valve and an expandable wall are disposed; moving the outer sheath in a first axial direction while the expandable wall and the replacement aortic valve are in a fixed position until the expandable wall is no longer disposed within the lumen of the outer sheath; and moving a distal end of the expandable wall towards a proximal end of the expandable wall, thereby causing a portion of the expandable wall to radially expand.

In a further aspect, the invention may be a method for implanting a replacement aortic valve, the method comprising: inserting a distal end of a catheter into a vasculature of a patient until a replacement aortic valve retained by the catheter is positioned at a desired location, the catheter including an outer sheath having a lumen within which the replacement aortic valve and an expandable wall are disposed; moving the outer sheath in a first axial direction while the expandable wall and the replacement aortic valve are in a fixed position until the expandable wall is no longer disposed within the lumen of the outer; temporarily stopping movement of the outer sheath in the first axial direction; radially expanding the expandable wall; after the expandable wall has been radially expanded, continuing movement of the outer sheath in the first axial direction until the replacement aortic valve is no longer disposed within the lumen of the outer sheath, the replacement aortic valve radially expanding as it exits the lumen of the outer sheath, thereby implanting the replacement aortic valve in the desired location.

In a still further aspect, the invention may be a catheter comprising: a handle assembly comprising a proximal slider assembly, a threaded handle insert operably coupled to the proximal slider assembly, and an outer handle operably coupled to the threaded handle insert, the proximal slider assembly comprising a proximal slider that is slidably coupled to a proximal slider housing; an outer sheath defining a lumen; an expandable wall assembly comprising an expandable wall having a distal end and a proximal end; a first tube having a first end operably coupled to the proximal slider and a second end operably coupled to the distal end of the expandable wall assembly; a second tube having a first end that is fixed with respect to the threaded handle insert and a second end operably coupled to the proximal end of the expandable wall assembly; wherein when the expandable wall is positioned outside of the lumen of the outer sheath, axial translation of the proximal slider alters the expandable wall between: (1) a first state in which the proximal and distal ends of the expandable wall are separated by a first distance; and (2) a second state in which the proximal and distal ends of the expandable wall are separated by a second distance, the first distance being greater than the second distance.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings:

FIG. 2A illustrates an exploded view of a distal tip assembly of the transfemoral catheter of FIG. 1A, in accordance with an exemplary embodiment of the present invention;

FIG. 2B is a close-up view of area IIB of FIG. 1B illustrating the distal tip assembly in cross-section, in accordance with an exemplary embodiment of the present invention;

FIG. 3 is a close-up view of area III of FIG. 1B, in accordance with an exemplary embodiment of the present invention;

FIG. 4 is a close-up view of area IV of FIG. 1B illustrating a cross-sectional view of a handle section of the transfemoral catheter of FIG. 1A, in accordance with an exemplary embodiment of the present invention;

FIG. 13A is a perspective view of a handle threaded insert of the transfemoral catheter of FIG. 1A, in accordance with an exemplary embodiment of the present invention;

FIG. 13B is a cross-sectional view taken along line XIIIB-XIIIB of FIG. 13A, in accordance with an exemplary embodiment of the present invention;

FIG. 15B is a cross-sectional view taken along line XVB-XVB of FIG. 15A, in accordance with an exemplary embodiment of the present invention;

FIG. 16 is a cross-sectional view of a proximal slider of the transfemoral catheter of FIG. 1A, in accordance with an exemplary embodiment of the present invention;

DETAILED DESCRIPTION

Figure 1A:
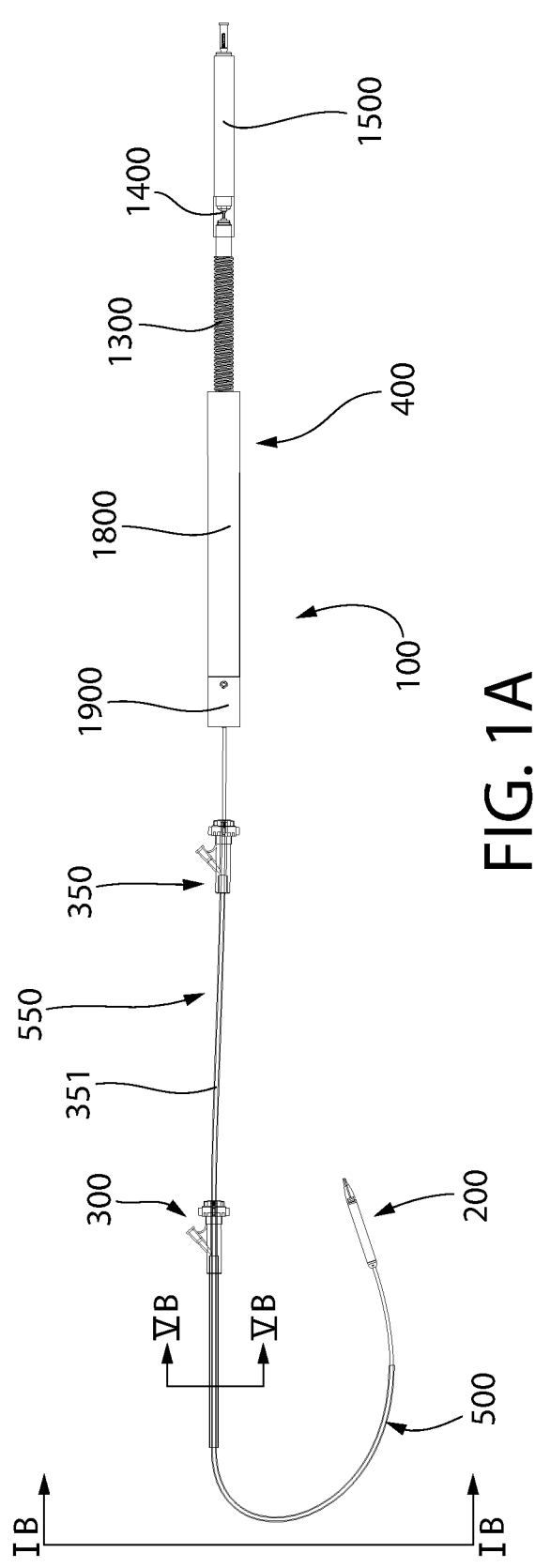
FIG. 1A illustrates a transfemoral catheter, in accordance with an exemplary embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used herein, the words, "proximal" and "distal," refer to directions closer to and further from, respectively, a physician implanting the replacement aortic valve using the transfemoral catheter described herein.

Figure 1B:
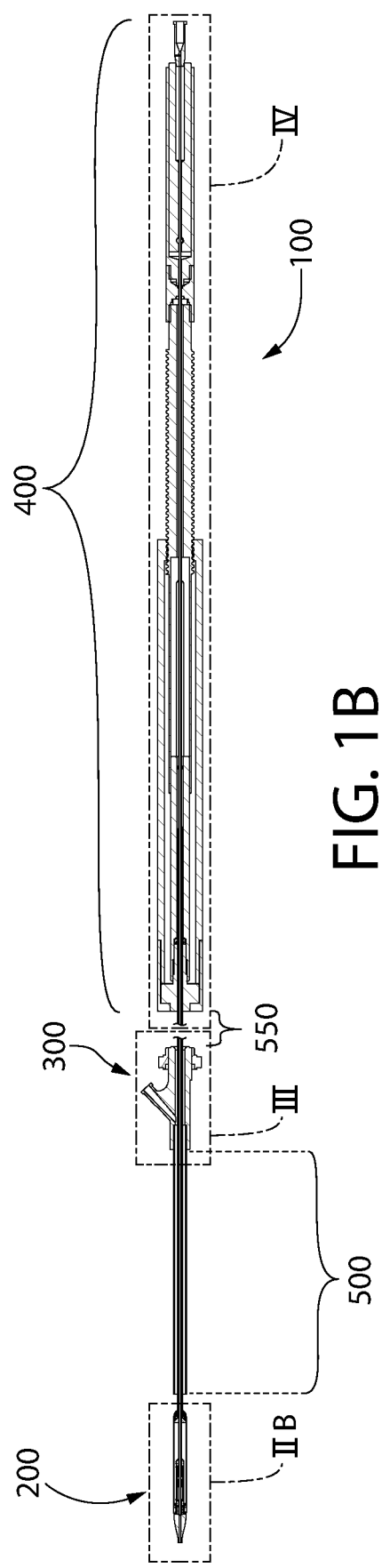
FIG. 1B illustrates a cross-section of the transfemoral catheter of FIG. 1A taken along line IB-IB, in accordance with an exemplary embodiment of the present invention.

Illustrated in FIG. 1A is a transfemoral catheter, generally designated as 100, in accordance with an exemplary embodiment of the present invention. Illustrated in FIG. 1B is a view of a partial cross-section of the transfemoral catheter 100 taken along a plane indicated by IB-IB in FIG. 1A, in accordance with an exemplary embodiment of the present invention. The transfemoral catheter 100 comprises a distal tip assembly 200, a connector 300 (also referred to as an introducer sheath), a stability sleeve 350, a handle section (assembly) 400, a first tubing assembly section 500, and a second tubing assembly section 550. FIG. 1B omits certain components, such as the stability sleeve 350, for purposes of fitting the figure on the page. Nonetheless, the stability sleeve 350 and its purpose will be readily understood from the description set forth herein.

Figure 6A:
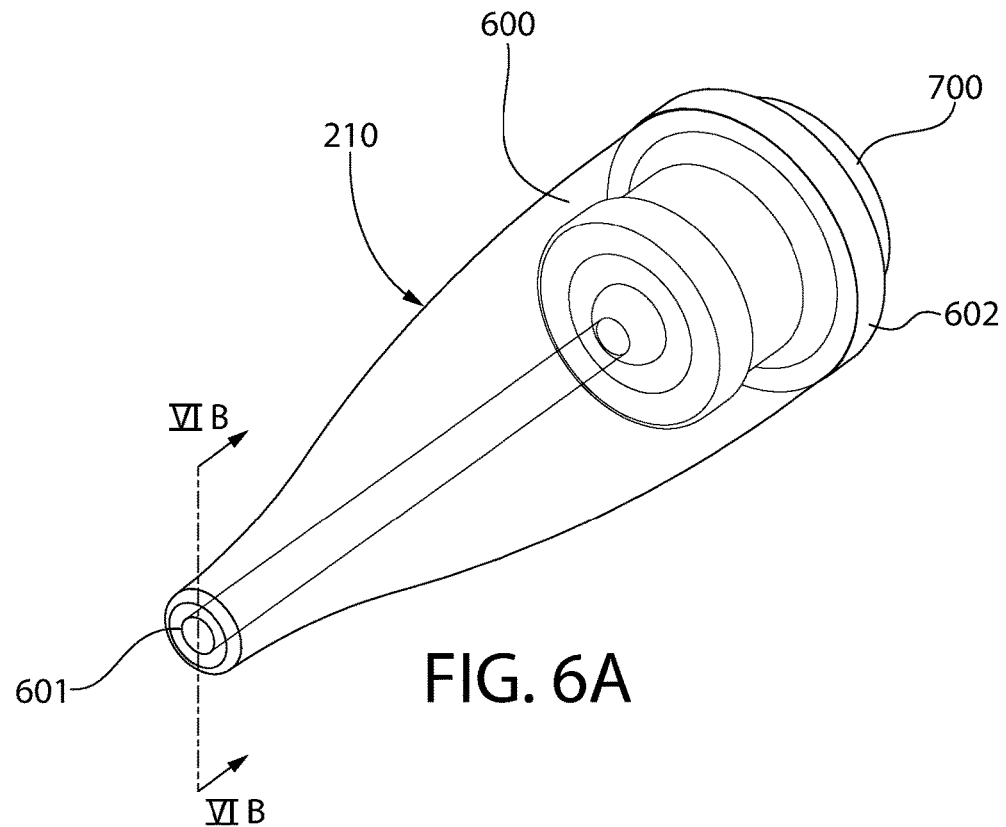
FIG. 6A illustrates a perspective view of a distal tip portion of the distal tip assembly of the transfemoral catheter of FIG. 1A, in accordance with an exemplary embodiment of the present invention.
Figure 6B:
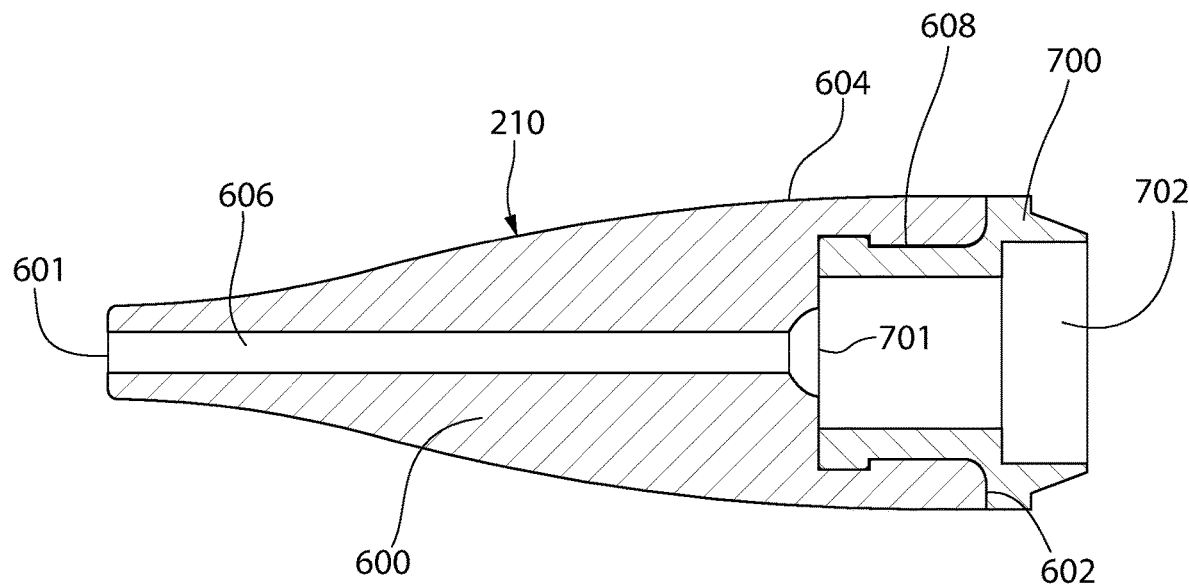
FIG. 6B is a cross-sectional view taken along line VIB-VIB of FIG. 6A, in accordance with an exemplary embodiment of the present invention.

Illustrated in FIG. 2A is an exploded view of the distal tip assembly 200 of the transfemoral catheter 100, in accordance with an exemplary embodiment of the present invention. Illustrated in FIG. 2B is a close-up view of the distal tip assembly 200 of the transfemoral catheter 100 in cross-section, in accordance with an exemplary embodiment of the present invention. The distal tip assembly 200 comprises a distal tip 210. A close-up, perspective view of the distal tip 210 is illustrated in FIG. 6A. A view of a cross-section of the distal tip 210 taken along a plane VIB-VIB is illustrated in FIG. 6B.

Referring to FIGS. 2A, 2B, 6A, and 6B, the distal tip 210 comprises an insert 700 and an overmolded tip 600. The overmolded tip 600 comprises an outer surface 604 that extends from a proximal end 602 to a distal end 601. The overmolded tip 600 comprises an inner lumen 606 extending from the distal end 601 toward the proximal end 602 and ending at an interior cavity 608 at the proximal end 602.

Figure 7A:
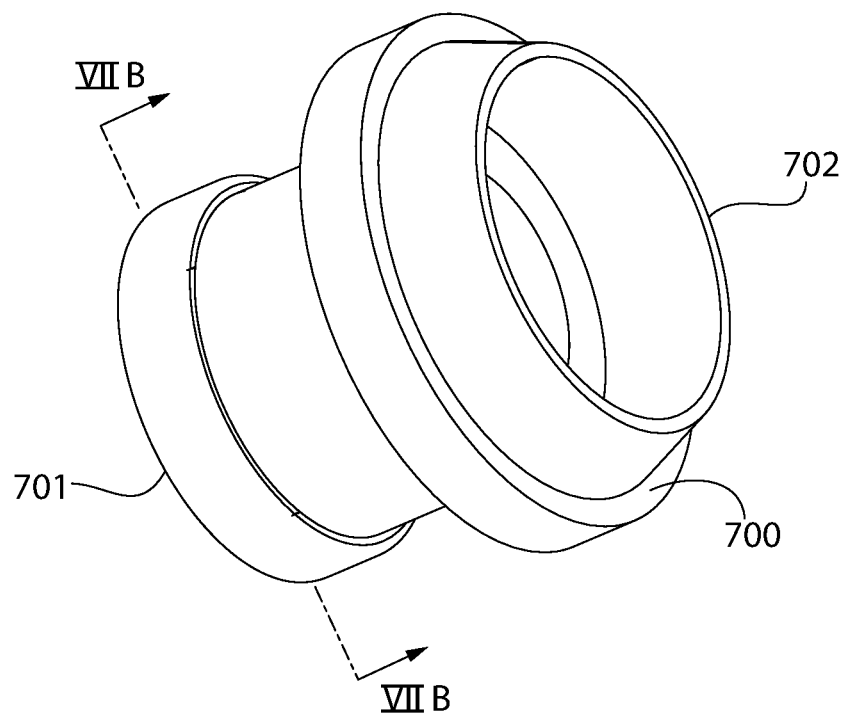
FIG. 7A is a perspective view of an insert of the distal tip portion of the distal tip assembly of the transfemoral catheter of FIG. 1A, in accordance with an exemplary embodiment of the present invention.
Figure 7B:
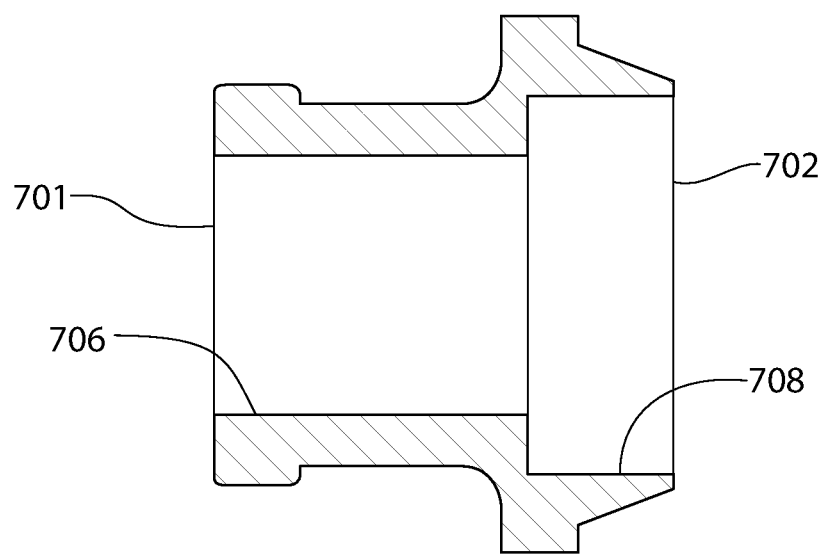
FIG. 7B is a cross-sectional view taken along line VIIB-VIIB of FIG. 7A, in accordance with an exemplary embodiment of the present invention.

Disposed in the interior cavity 608 is the insert 700 comprising a distal end 701 and a proximal end 702. FIG. 7A illustrates a close-up, perspective view of the insert 700, in accordance with an exemplary embodiment of the present invention. FIG. 7B illustrates a view of a cross-section of the insert 700 taken along a plane VIIB-VIIB of FIG. 7A, in accordance with an exemplary embodiment of the present invention.

The insert 700 comprises an inner lumen 706 extending from the distal end 701 toward the proximal end 702 and ending at an interior cavity 708 at the proximal end 702. In an exemplary embodiment, disposed within the interior cavity 706 are threads (not shown in these views).

Figure 8A:
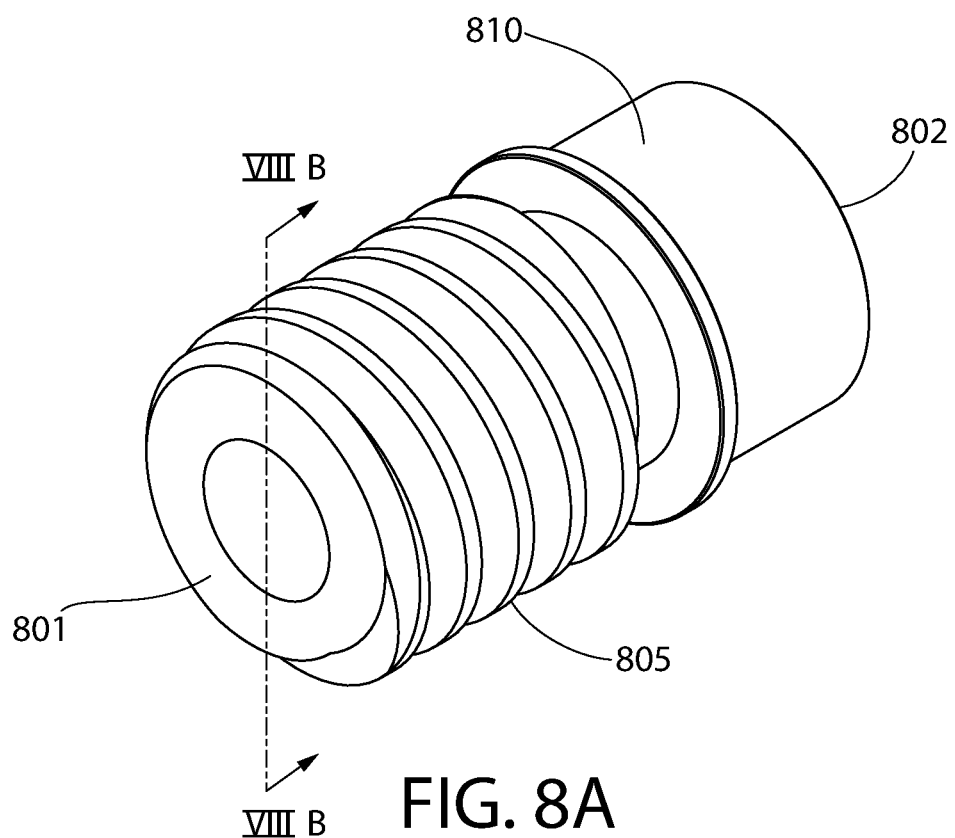
FIG. 8A is a perspective view of a distal insert of an expandable wall assembly of the transfemoral catheter of FIG. 1A, in accordance with an exemplary embodiment of the present invention.
Figure 8B:
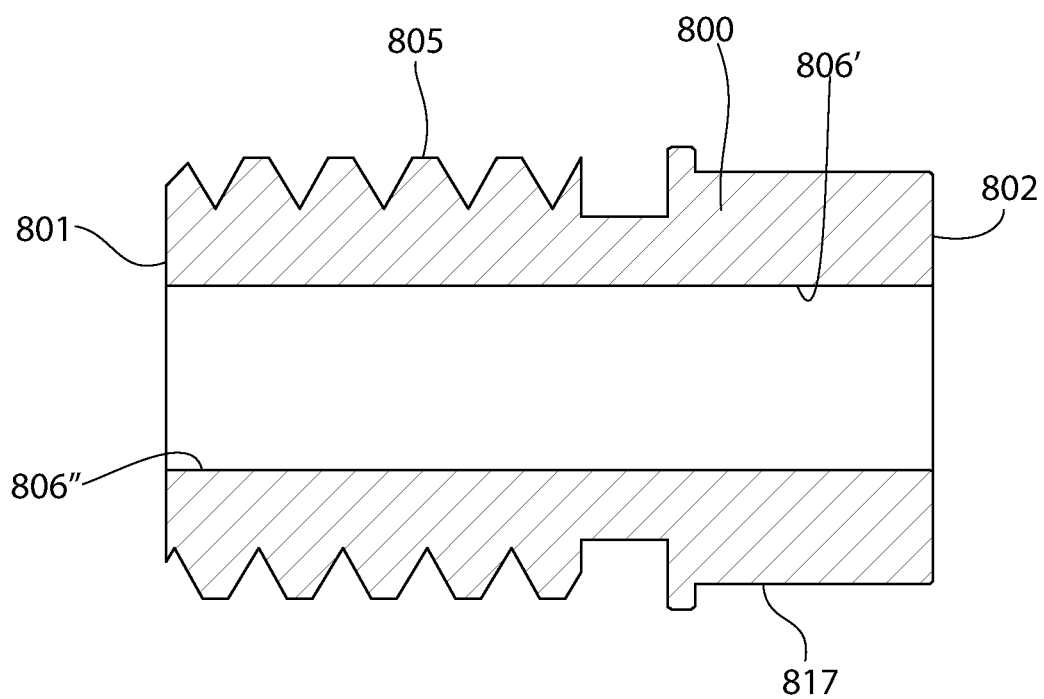
FIG. 8B is a cross-sectional view taken along line VIIIB-VIIIB of FIG. 8A, in accordance with an exemplary embodiment of the present invention.

Referring again to FIGS. 2A and 2B, the distal tip assembly 200 further comprises an expandable wall assembly 220 comprising an insert 800 (also referred to as distal threads), an expandable wall 900, and a proximal insert 1000. A close-up, perspective view of the insert 800 is illustrated in FIG. 8A. A view of a cross-section of the insert 800 taken along a plane VIIIB-VIIIB is illustrated in FIG. 8B.

The insert 800 comprises a distal end 801, a proximal end 802, threads 805 disposed on an outer wall of the insert 800 at the distal end 801 thereof, and a cylindrical wall section 810 at the proximal end 802. The threaded distal end 801 is configured for being inserted into the interior cavity 708 of the insert 700 and secured therein. The insert 800 comprises an inner lumen 806 extending from the distal end 801 to the proximal end 802 of the insert 800.

Although not illustrated, the interior wall of the interior cavity 706 of the insert 700 may comprise threads for engaging with the threads 805 of the insert 800. In some embodiments, the insert 800 may not include the threads 805, and the insert 700 may not include threads in the interior cavity 706 of the insert 700. In such embodiments, the outer wall of the distal end 801 of the insert 800 is disposed within the interior cavity 706 of the insert 700 and secured therein, such as by a tight or interference fit or by the use of an adhesive, solvent bond, welding, or the like.

Referring again to FIG. 2B, the transfemoral catheter 100 further comprises a first tube 230 comprising a distal end 231. Disposed about the first tube 230 at its distal end 231 is a crimp tube 235 that secures the distal end 231 of the first tube 230 within the lumen 806 of the insert 800. In some embodiments, the crimp tube 235 may be omitted, and the distal end 231 of the first tube 230 may be directly secured within the lumen 806 of the insert 800, such as by an adhesive, solvent bond, weld, etc.

In one particular embodiment, the first tube 230 may comprise or be formed entirety from nitinol, which is a mixture of nickel and titanium present in roughly equal atomic percentages. Nitinol may be a preferable material due to its shape memory and superelasticity. When formed from nitinol, the first tube 230 may be crimped within the crimp tube 235. In other embodiments, the first tube 230 may comprise stainless steel, titanium, or the like. In some embodiments, the first tube 230 may comprise a material which does not require a crimp tube 235, for example, titanium. In some embodiments, wherein the first tube 230 comprises a material that does not require a crimp tube 235, the first tube 230 may be welded directly to the insert 800. In some embodiments, the crimp tube 235 may be welded within the lumen 806 of the insert 800.

Figure 9A:
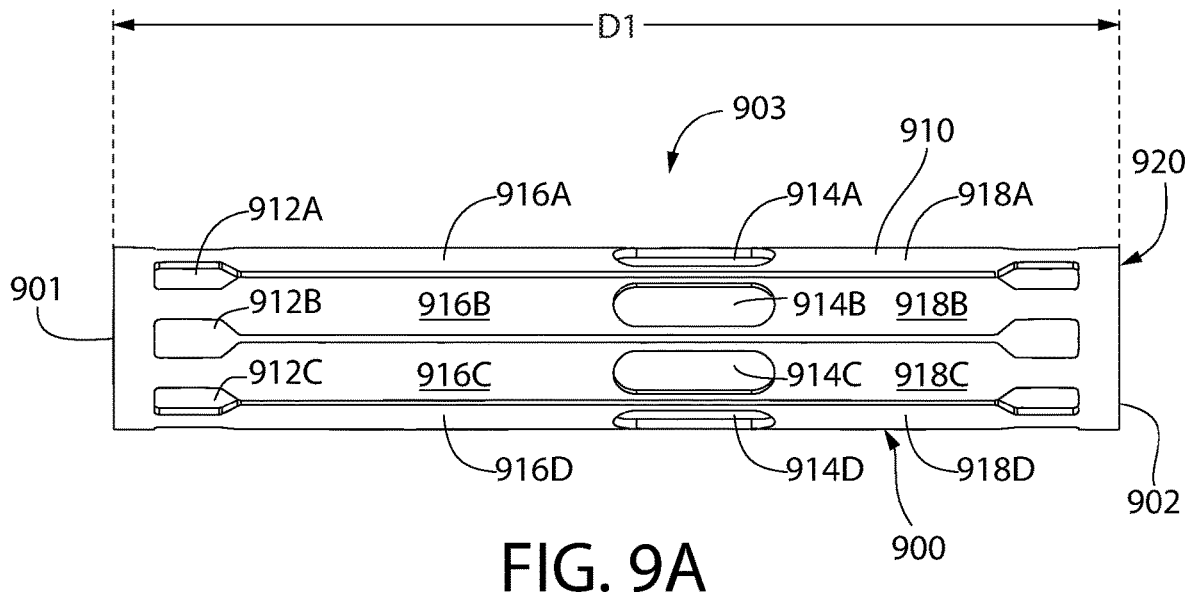
FIG. 9A illustrates an expandable wall of the expandable wall assembly of the transfemoral catheter of FIG. 1A in a biased state, in accordance with an exemplary embodiment of the present invention.
Figure 9B:
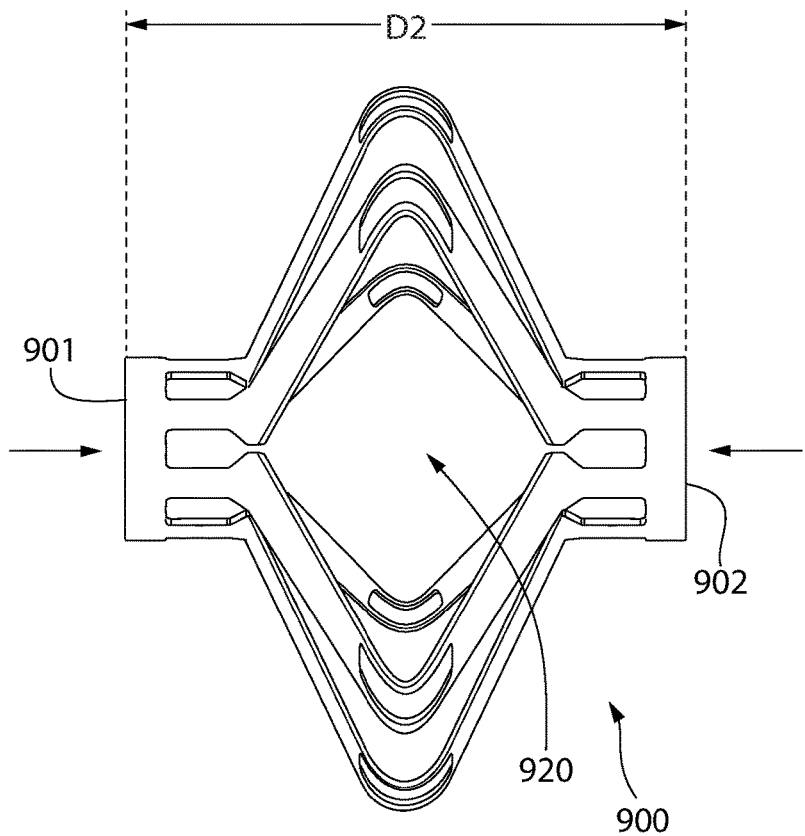
FIG. 9B illustrates the expandable wall of FIG. 9A in an axially compressed state, in accordance with an exemplary embodiment of the present invention.

FIG. 9A illustrates the expandable wall 900 in its biased, non-deformed state. When no pressure or forces are applied onto the expandable wall 900, it takes the form as depicted in FIG. 9A. However, as described in more detail below, when a force is applied onto the expandable wall 900 in opposing axial directions simultaneously, the expandable wall 900 will compress axially and expand radially, as illustrated in FIG. 9B. Thus, the expandable wall 900 is alterable between a first state, which is the biased state, and a second state, which is the compressed state, in which the expandable wall is compressed axially and expanded radially.

The expandable wall 900 comprises a tube 910 extending from a distal end 901 to a proximal end 902 and having an interior cavity 920. The interior cavity 920 at the distal end 901 of the tube 900 is sized to be disposed over the outer wall 817 of the insert 800 at its proximal end 802. In some embodiments, an adhesive may be used to secure the tube 910 to the insert 800 although such adhesive is not required in all embodiments. In another exemplary embodiment, the insert 800 may be formed from a metal, and the expandable wall 900 may be formed from a metal. In such embodiment, the insert 800 may be soldered or welded to the expandable wall 900.

The tube 910 comprises a plurality of cutouts 912A, 912B, 912C, etc. formed therein near the distal end 901. The tube 910 further comprises a plurality of cutouts 914A, 914B, 914C, 914D, etc. formed therein at or near a midpoint 903 of the tube 910. The cutouts 914A-D may be located closer to the proximal end 902 of the tube 910 than to the distal end 901 of the tube 910 or closer to the distal end 901 of the tube 910 than the proximal end 902 of the tube 910, although this is not required in all embodiments. In the exemplary embodiment illustrated, the cutouts 912A, 912B, 912C, etc. each have a double-ended oar shape, and the cutouts 914A, 914B, 914C, 914D, etc. each have an oval shape. As a result of the cutouts 912A, 912B, 912C, 912D, etc. and 914A, 914B, 914C, 914D, etc., the tube 910 comprises a plurality of bendable fingers 916A, 916B, 916C, 916D, etc. that are thinner at a distal end of the tube 910 and a proximal end of the tube 910 and wider toward the middle 903 of the tube 910.

The thin ends of the fingers 916A, 916B, 916C, 916D, etc. allow the fingers 916A, 916B, 916C, 916D, etc. to bend at the distal and proximal ends 901, 902 of the tube 910. The cutouts 914A, 914B, 914C, 914D, etc. allow the fingers 916A, 916B, 916C, 916D, etc. to bend at or near the middle 903 of the tube 910.

The bending of the fingers 916A-D is best shown in FIG. 9B, where the expandable wall 900 is illustrated in the axially compressed state. Specifically, when an axial force is applied onto the expandable wall 900 at either or both of the proximal and distal ends 901, 902 thereof, the expandable wall 900 compresses axially and expands radially due to the bending of the fingers 916A-D as described herein. As will be better understood from the description below, the expandable wall 900 in the axially compressed state is able to reduce or prevent movement of a replacement aortic valve during installation into a patient. Specifically, because the expandable wall 900 expands radially, it blocks a replacement aortic valve from becoming a projectile and moving axially past the radially expanded portion of the expandable wall 900.

Thus, the expandable wall 900 is alterable between: (1) a first state in which the proximal and distal ends 901, 902 of the expandable wall 900 are separated by a first distance D1; and (2) a second state in which the proximal and distal ends 901, 902 of the expandable wall 900 are separated by a second distance D2, the first distance D1 being greater than the second distance D2. Thus, the first state is the biased state where the expandable wall is not axially compressed, as shown in FIG. 9A and the second state is the axially compressed and radially expanded state, as shown in FIG. 9B.

Figure 10A:
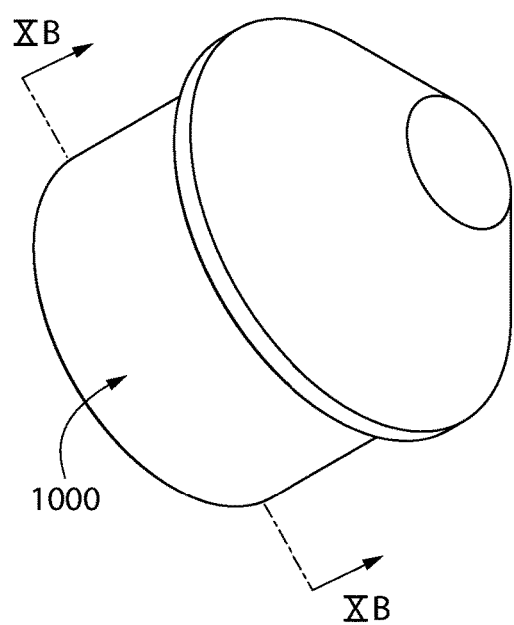
FIG. 10A is a perspective view of a proximal insert of the expandable wall assembly of the transfemoral catheter of FIG. 1A, in accordance with an exemplary embodiment of the present invention.
Figure 10B:
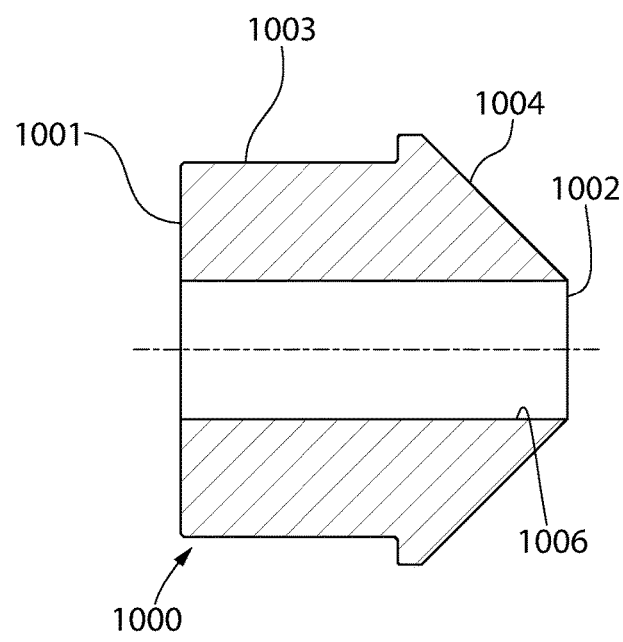
FIG. 10B is a cross-sectional view taken along line XB-XB of FIG. 10A, in accordance with an exemplary embodiment of the present invention.

A close-up, perspective view of the proximal insert 1000 is illustrated in FIG. 10A. A cross-section of the insert 1000 taken along a plane XB-XB in FIG. 10A is illustrated in FIG. 10B. The insert 1000 comprises a distal end 1001, a proximal end 1002, a cylindrical outer surface 1003 at the distal end 1001 of the insert 1000, a cone-shaped outer surface 1004 at the proximal end 1002 of the insert 1000, and an interior lumen 1006 extending from the distal end 1001 to the proximal end 1002 of the insert 1000.

The cylindrical outer surface 1003 is sized to be disposed within the interior cavity 920 at the proximal end 902 of the expandable wall 900. The insert 1000 is secured to the expandable wall 900. In the exemplified embodiment, the expandable wall 900 and the insert 100 are fixed together by welding spots (or raised dots) on the cylindrical outer surface 1003 in the cutouts 912A-C, thereby pinning the distal and proximal collars of the tube 910 between the welded dots and the shoulder formed between the cylindrical outer surface 1003 and the cone-shaped outer surface 1004. In an alternative embodiment, an adhesive may be used to secure the insert 1000 within the expandable wall 900. In another exemplary embodiment, the insert 1000 may be formed from a metal, and the expandable wall 900 may be formed from a metal. In such embodiment, the insert 1000 may be soldered or welded to the expandable wall 900.

Because the distal end 231 of the first tube 230 is secured to the insert 800, which forms a part of the expandable wall assembly 220, translation of the first tube 230 causes translation of the tip assembly 210 and the expandable wall assembly 220. Such movement of the distal end 231 of the first tube 230, including how it is achieved and the effect that it has on the remainder of the transfemoral catheter 100, is further described below.

Referring again to FIGS. 2A and 2B, the transfemoral catheter 100 further comprises a second tube 240, a pusher 250, an outer sheath or sheath 260, a proximal end cap 1100, and a proximal top cap 1200. The second tube 240, or a portion thereof (which may be formed by a separate tube that is coupled to the second tube 240) may be a laser cut hypotube to provide the second tube 240 with the flexibility required during operation. A first distal end portion 241 of the second tube 240 is secured within the lumen 1006 of the proximal insert 1000. A second distal end portion 242 of the second tube 240 is secured within a lumen of the pusher 250. The second tube 240 extends into the expandable wall 900 and terminates less than halfway along the length of the expandable wall 900. In this way, the second tube 240 restricts the expandable wall 900 from expanding beyond the dimension desired for proper placement of the valve. Overexpansion would place too much stress on the cutouts/joints 912A-D and 914A-D.

In an exemplary embodiment, the first distal end portion 241 of the second tube 240 is secured within the lumen 1006 of the proximal insert 1000 by an adhesive, and the second distal end portion 242 of the second tube 240 is secured with the lumen of the pusher 250 by an adhesive. In another exemplary embodiment, the second tube 240, the proximal insert 1000, and the pusher 250 may be formed from a metal. In such embodiment, the first distal end portion 241 of the second tube 240 may be welded or soldered within the lumen 1006 of the proximal insert 1000, and the second distal end portion 242 of the second tube 240 may be welded or soldered with the lumen of the pusher 250. Other techniques for coupling the various components together may be possible and would be appreciated by persons skilled in the art.

Figure 11A:
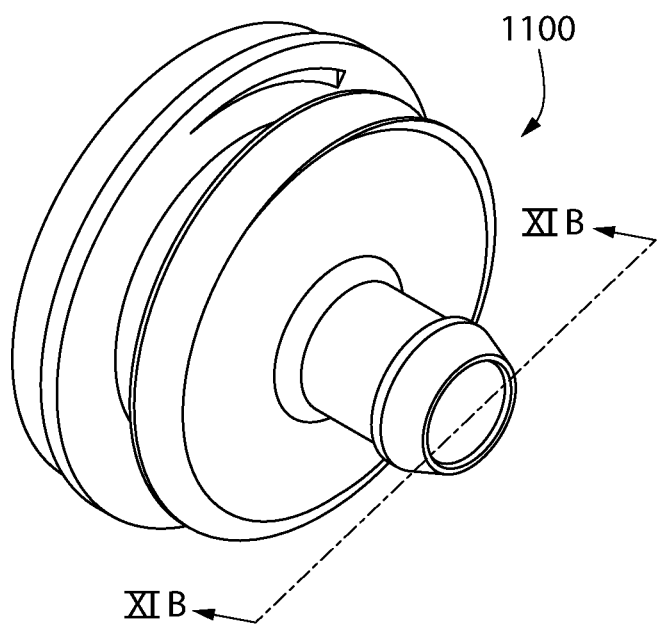
FIG. 11A is a perspective view of a proximal end cap of the transfemoral catheter of FIG. 1A, in accordance with an exemplary embodiment of the present invention.
Figure 11B:
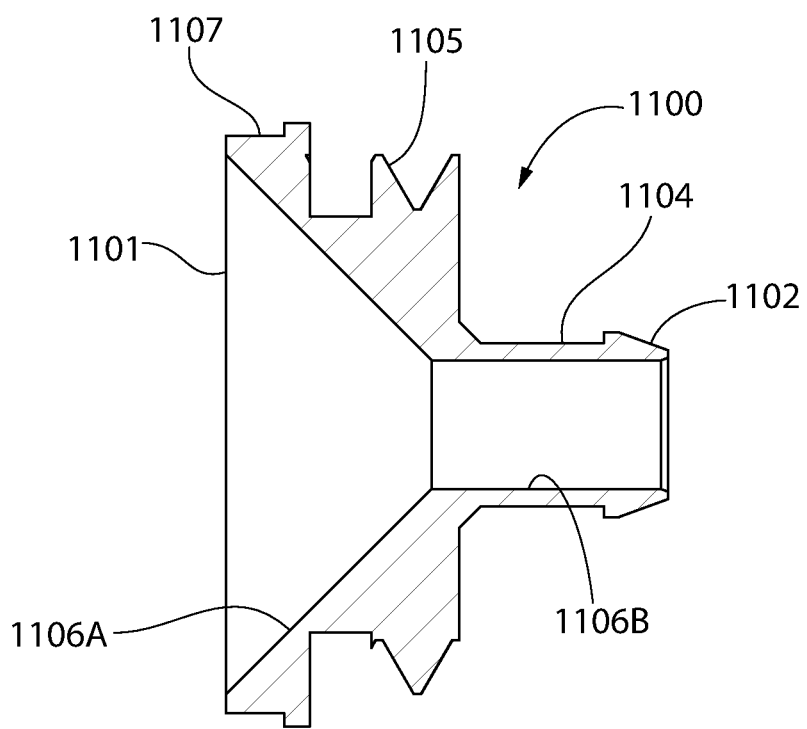
FIG. 11B is a cross-sectional view taken along line XIB-XIB of FIG. 11A.

FIG. 11A illustrates a close-up, perspective view of the proximal end cap 1100, in accordance with an exemplary embodiment of the present invention. FIG. 11B illustrates a cross-sectional view of the proximal end cap 1100 taken along a plane XIB-XIB shown in FIG. 11A, in accordance with an exemplary embodiment of the present invention.

The proximal end cap 1100 comprises a distal end 1101, a proximal end 1102, and a cone-shaped inner lumen 1106A extending proximally and tapering inwardly toward the proximal end 1102 from the distal end 1101. The proximal end cap 1100 further comprises a cylindrical interior lumen 1106B that terminates at the proximal end 1102.

The proximal end cap 1100 comprises an outer surface that is generally separated into three regions. A first region 1107 forms a cylindrical surface that is disposed and secured within the sheath 260 at its proximal end 262. A second region 1105 comprises threads. A third region 1104 comprises a generally cylindrical stem.

Figure 12A:
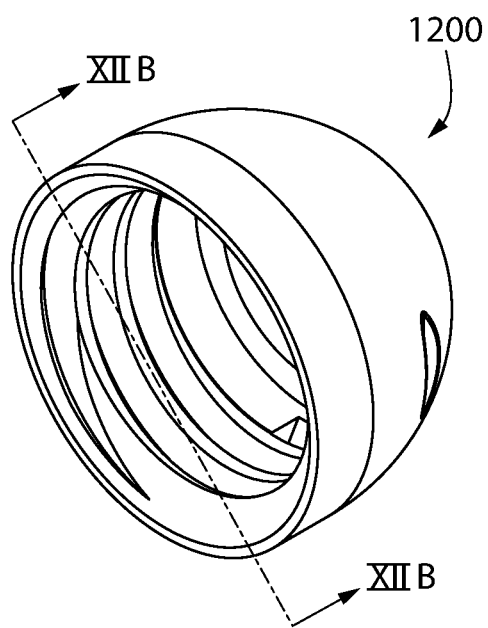
FIG. 12A is a perspective view of a proximal top cap of the transfemoral catheter of FIG. 1A, in accordance with an exemplary embodiment of the present invention.
Figure 12B:
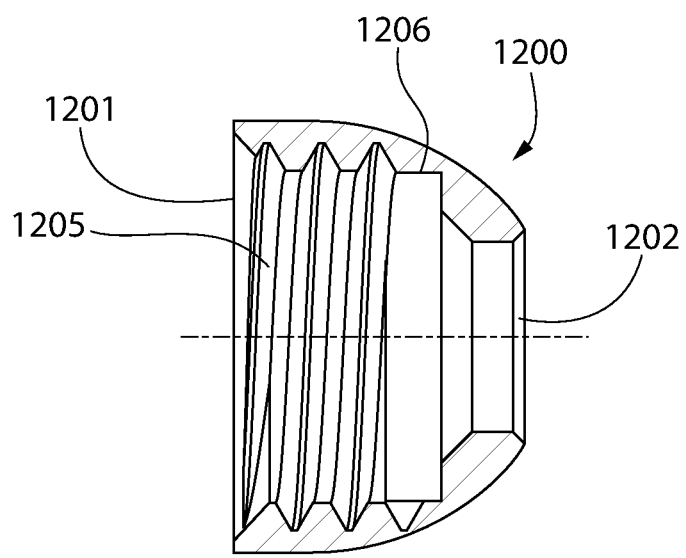
FIG. 12B is a cross-sectional view taken along line XIIB-XIIB of FIG. 12A, in accordance with an exemplary embodiment of the present invention.

FIG. 12A illustrates a close-up, perspective view of the proximal top cap 1200, in accordance with an exemplary embodiment of the present invention. FIG. 12B illustrates a cross-sectional view of the proximal top cap 1200 taken along a plane XIIB-XIIB of FIG. 12A, in accordance with an exemplary embodiment of the present invention.

The proximal top cap 1200 comprises a distal end 1201, a proximal end 1202, and an inner lumen 1206 extending from the distal end 1201 to the proximal end 1202. Disposed on an inner surface of the inner lumen 1206 are threads 1205 for engaging the threads 1105 of the proximal end cap 1100 to secure the proximal top cap 1200 to the proximal end cap 1100 and to the sheath 260. Referring again to FIG. 2B, the second tube 240 is slidably disposed within the lumen 1106B of the proximal end cap 1100. The pusher 250 is secured to the second tube 240 at the second distal end portion 242 of the second tube 240 and is spaced from the proximal end 902 of the expandable wall 900 by a distance sized to accommodate a replacement aortic valve (described below).

In some embodiments, the second tube 240 is welded to the pusher 250 at the distal end of pusher 250. In alternative embodiments, the second tube 240 may comprise multiple tubes having different dimensions. In some embodiments, the second tube 240 may comprise a first sub-tube and a second sub-tube. In some embodiments, the diameter of second sub-tube may be greater than the diameter of first sub-tube. In some embodiments, the first sub-tube and second sub-tube are welded to the pusher 250 with both being approximately halfway inside the pusher 250.

The pusher 250 comprises a distal outer surface 253, generally cylindrical in shape at a distal end 251, and a proximal outer surface 254 at a proximal end 252. The outer surface 253, 254 of the pusher 250 is cone shaped and is sized to fit within the inner lumen 1106A of the proximal end cap 1100.

In one state, typically prior to operation, the second tube 240 and the pusher 250 are both disposed within the outer sheath 260. As will be understood from the description below, particularly with reference to FIGS. 22A-28B, the outer sheath moves relative to the second tube 240 and the pusher 250 during deployment of the replacement aortic valve. Thus, the pusher 250 and the expandable wall 900 hold the replacement aortic valve in place while the sheath 260 moves axially in the proximal direction to expose the replacement aortic valve so that it can be deployed into the patient's heart. Thus, in the exemplified embodiment described and illustrated herein, when deploying the replacement aortic valve, the second tube 240 and the pusher 250 remain in a fixed or static position, while the outer sheath 260 is translated proximally such that pusher 250 is becomes exposed from the distal end 261 of outer sheath 260 via the movement of the outer sheath 260.

The first tube 230 is attached to the distal end of the tip assembly 200 and the second tube 240 is secured to the proximal insert 1000. The first and second tubes 230, 240 are not fixed to one another, and thus the first tube 230 is slidably disposed within the second tube 240. Specifically, the first tube 230 can slide relative to the second tube 240 and this is done to achieve the axial compression/radial expansion of the expandable wall 900 mentioned above. Specifically, the expandable wall 900 expands (FIG. 9A) and contracts (FIG. 9B) because the first tube 230 and the expandable wall 900 are attached to the tip assembly 200. Thus, when the first tube 230 is pulled back in the proximal direction, the second tube 240 remains stationary and the tip assembly 200 moves in the proximal direction towards the proximal insert 1000, thereby causing axial compression and radial expansion of the expandable wall 900. The expandable wall 900 folds or contracts during this process, which enables the expandable wall 900 to be deployed as described further herein below.

Stated another way, movement of the first tube 230 relative to the second tube 240 causes the expandable wall 900 to crumple (axially compress and radially expand) or revert to its un-crumpled (biased or uncompressed) state. In the relative positions illustrated in FIG. 2B, if the distal end 231 of the first tube 230 is moved proximally toward the distal end 241 of the second tube 240, the expandable wall 900 compresses axially and expands radially as the fingers 916A, 916B, 916C, 916D, etc. fold as shown in FIG. 9B. The axial compression of the expandable wall 900 is limited by the contact of the proximal end of the insert 800 and the distal end of the second tube 240 as the insert 800 moves proximally during axial compression of the expandable wall 900. If the distal end 231 of the first tube 230 is moved distally away from the distal end 241 of the second tube 240, the expandable wall 900 straightens and returns to its biased or uncompressed state as the fingers 916A, 916B, 916C, 916D, etc. straighten (FIG. 9A). This will be described again with specific reference to FIGS. 24A and 24B.

Figure 5A:
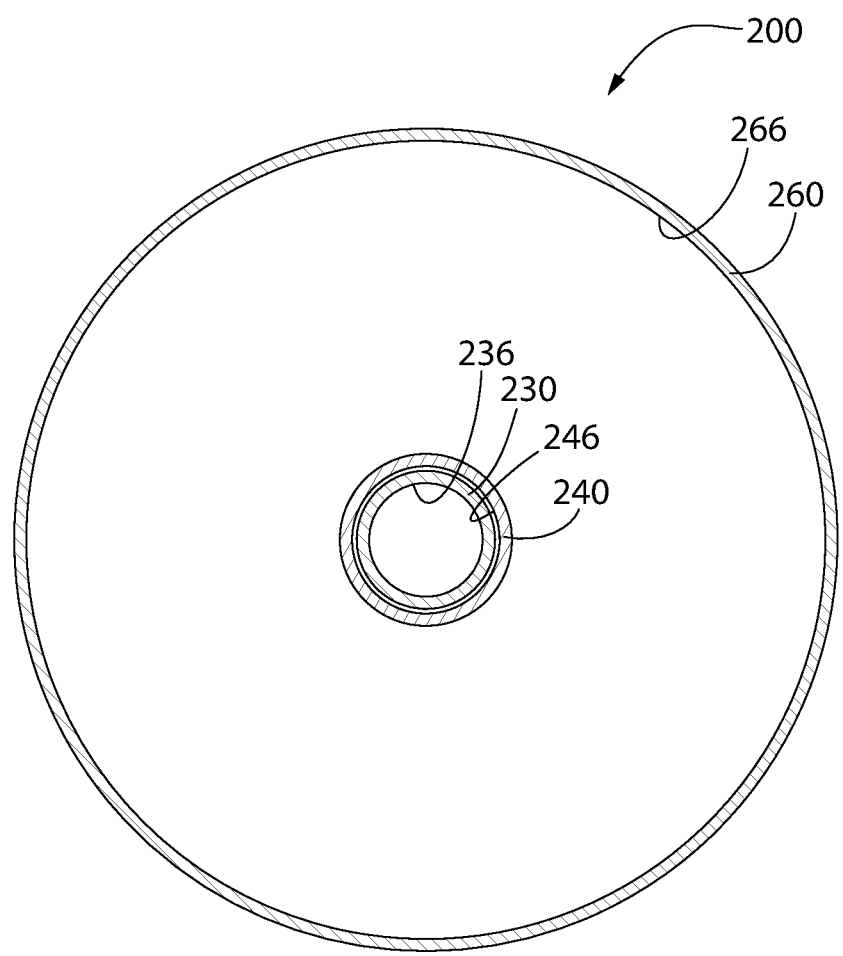
FIG. 5A is a cross-sectional view taken along line VA-VA in FIG. 2B, in accordance with an exemplary embodiment of the present invention.

Referring now to FIG. 5A, there is illustrated a view of a cross-section of the tip assembly 200 taken along a section VA-VA illustrated in FIG. 2B, in accordance with an exemplary embodiment of the present invention. As seen in the figure, the tip assembly 200 comprises the first tube 230, the second tube 240, and the outer sheath 260. The first tube 230 comprises an interior lumen 236, the second tube 240 comprises an interior lumen 246, and the outer sheath 260 comprises an interior lumen 266. Within the tip assembly 200, at least a portion of the first tube 230 is slidably disposed with at least a portion of the interior lumen 246 of the second tube 240. In the tip assembly 200, both tubes 230 and 240 are disposed with the lumen 266 of the sheath 260. As seen in FIG. 2B, the distal end 231 of the first tube 230 is disposed distally of the first distal end portion 241 of the second tube 240.

Referring again to FIG. 2B, the transfemoral catheter 100 further comprises a braided shaft 270, a distal end 271 of which is disposed over the stem 1104 of the proximal end cap 1100. A crimp 274 secures the distal end 271 of the braided shaft 270 to the stem 1104. Other exemplar embodiments of the transfemoral catheter 100 in which the crimp 274 is omitted are contemplated. The transfemoral catheter 100 also includes a stability tube 351 that is associated with and forms a part of the stability sleeve 350.

Figure 5B:
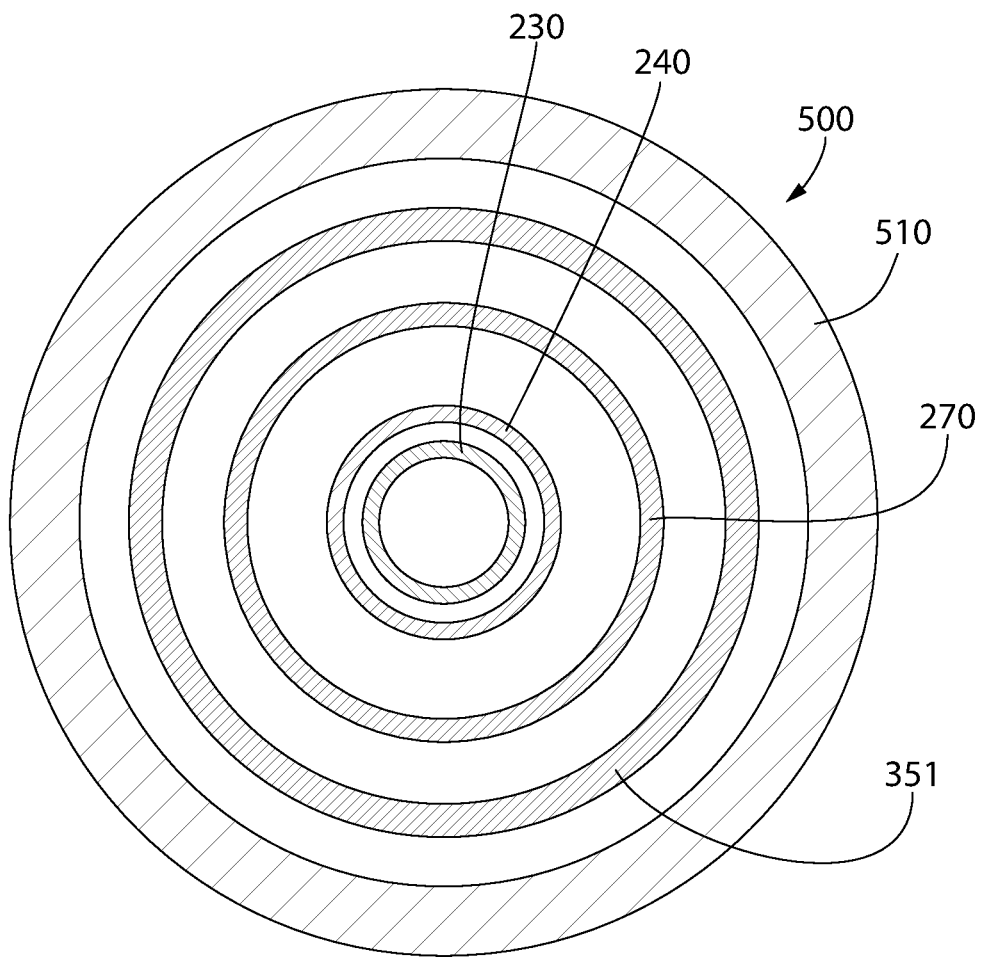
FIG. 5B is a cross-sectional view taken along line VB-VB of FIG. 1A, in accordance with an exemplary embodiment of the present invention.

Referring now to FIG. 5B, there is illustrated a view of a cross-section of the first tubing assembly section 500 taken along a section VB-VB illustrated in FIG. 1A, in accordance with an exemplary embodiment of the present invention. As seen in the figure, the first tubing assembly section 500 comprises the tubes 230 and 240 and the braided shaft 270 and further comprises the stability tube 351 and an outer sheath 510 that is associated with the connector 300, described below. The braided shaft 270 comprises an interior lumen 276. The first and second tubes 230 and 240 are slidably disposed within the interior lumen 276 of the braided shaft 270. The outer sheath 510 is slidable along the stability tube 351 and the stability tube 351 is slidable along the braided shaft 270.

Referring now to FIG. 3, there is illustrated an exemplary embodiment of the connector 300, in accordance with an exemplary embodiment of the present invention. The connector comprises a distal end 301, a proximal end 302, and a body 310. The body 310 comprises an interior lumen 306 disposed at the distal end 301 of the connector 300, and an interior lumen 308 extending from the interior lumen 306 to the proximal end 302 of the connector 300. The interior lumens 306 and 308 are in fluid communication with one another.

Disposed at a midsection 303 of the connector 300 is an arm 320. A distal end 321 of the arm 320 connects with the body 310 of the connector 300. Disposed with the arm 320 is a lumen 326 that extends from the distal end 321 of the arm 320 to a proximal end 322 of the arm 320. The lumen 326 opens to the outside of the connector 300 at the proximal end 322 of the arm 320 and to the interior lumen 306 at the distal end 321 of the arm 320. The interior lumen 308 is sealed between the distal end 321 of the arm 320 and the proximal end 302 of the connector 300 to prevent communication of fluid between the lumen 308 at the outside of the connector 300 via the proximal end 302 of the connector. The connector 300 is moveable relative to the braided shaft 270. A lock nut 330 is coupled to a proximal portion of the connector 300. The lock nut 330 is rotatable relative to the connector 300 such that rotation of the lock nut 330 in one direction will lock the connector 300 to the braided shaft 270 to prevent the connector 300 from moving relative to the braided shaft 270. Specifically, there is a seal (not shown) that squeezes down around the braided shaft 270 when the lock nut 330 is rotated clockwise a sufficient amount. If the lock nut 330 is then rotated counterclockwise, the connector 300 becomes disengaged or unlocked relative to the braided shaft 270 so that the connector 300 is free to move relative to the braided shaft 270.

Extending from the distal end 301 of the connector 300 is the outer sheath 510. The outer sheath 510 comprises a distal end 511, a proximal end 512, and a wall 515 extending from the distal end 511 to the proximal end 512. The wall 515 at the proximal end 512 of the outer sheath 510 extends into and is disposed within the interior lumen 306 of the connector 300. During use of the transfemoral catheter 100, the distal end 511 of the outer sheath 510 is disposed within the vasculature of a patient. Medication may be administered within the patient's vasculature by way of a syringe or drip bag attached to the proximal end 322 of the arm 320 of the connector 300. The medication enters the lumen 326 of the arm 320, flows into the lumen 308 of the connector 320, flows into the lumen 516 of the outer sheath 510, and enters the patient's vasculature via an opening at the distal end 511 of the outer sheath 510. Such medication may be antibiotics, anti-coagulation medication, or any other medication useful in heart-valve replacement, etc.

The braided shaft 270 passes through the lumen 308 and extends through the proximal end 302 of the connector 300. The portion of the braided shaft 270 proximal to the connector 300 forms part of the second tubing assembly section 550. The cross section of the second tubing assembly section 550 is the same as that illustrated in FIG. 5B except that the outer sheath 510 is omitted in the second tubing assembly section 550. Thus, a distal end 601 (FIG. 3) of the second tubing assembly section 550 connects (directly or indirectly) to the connector 300, and a proximal end 602 (FIG. 4) of the second tubing assembly section 550 connects (directly or indirectly) to the handle section 400. The second tubing assembly section 550 may be slidable over the braided shaft 270.

Referring to FIGS. 1A and 3, as noted above the transfemoral catheter also includes the stability sleeve 350. The stability sleeve 350 has an identical structure to the connector 300, except that the stability tube 351 has a smaller diameter than the outer sheath 510 so that the stability tube 351 is disposed within the lumen of the outer sheath 510. The stability tube 351 is much longer than the outer sheath 510, and thus the connector 300 and the outer sheath 510 are located along the stability tube 351. The connector 300 is able to slide axially along the stability tube 351. The stability tube 351 forms a track within which the braided shaft 270 moves during translation of the braided shaft 270 and the outer sheath 260, described in more detail below. The stability sleeve 350, and specifically the stability tube 351 thereof, prevents the braided shaft 270 from curling and interfering with a patient's organs by ensuring that it follows a desired movement path within the patient's body. Except as described herein, the description of the connector 300 is applicable to the stability sleeve 350 as well.

Referring now to FIG. 4, there is illustrated a cross-sectional view of the handle section 400 of the transfemoral catheter, 100 in accordance with an exemplary embodiment of the present invention. The handle section or assembly 400 comprises an outer handle 1800, an outside cap 1900 disposed at distal end 1801 of the outer handle 1800. The handle assembly 400 further comprises a distal slider 2000, an inner ring 1700, and a handle threaded insert 1300. The handle assembly 400 also comprise a seal housing 1400, a proximal slider housing 1500, and a proximal slider 1600. There may also be a reinforcing tube in this section of the handle 400. Such a reinforcing tube may sit inside the lumens of the distal slider 2000, which slides into the threaded handle as the distal slider 2000 moves proximally.

A close-up, perspective view of the handle threaded insert 1300 is illustrated in FIG. 13A. A cross-section view of the handle threaded insert 1300 taken along line XIIIB-XIIIB of FIG. 13A is illustrated in FIG. 13B. The handle threaded insert 1300 comprises a distal end 1301, a proximal end 1302, and an outer wall 1310 extending from the distal end 1301 to the proximal end 1302. The outer wall 1310 comprises a first smooth section 1311, a mid-section 1313, a threaded section 1315, and a second smooth section 1312.

The mid-section 1313 is located approximately at the midpoint of the handle threaded insert 1300. The first smooth section 1311 extends from the distal end 1301 to the mid-section 1313. The threaded section 1315 includes and extends from the mid-section 1313 toward the proximal end 1302 but ends before the proximal end 1302. The second smooth section 1312 is disposed at the proximal end 1302. Disposed in the outer wall 1310 along the first smooth section 1311 and extending longitudinally is a slot 1320. The slot 1320 begins proximally to the distal end 1301 and ends distally to the mid-section 1313.

Disposed within the handle threaded insert 1300 in the first smooth section 1311 and in the midsection 1313 is a first longitudinal lumen 1306. Disposed within the handle threaded insert 1300 in the threaded section 1315 and in the second smooth section 1312 is a second longitudinal lumen 1308, the second longitudinal lumen 1308 having a smaller cross-sectional area than the first longitudinal lumen 1306. The first and second longitudinal lumens 1306, 1308 communicate with one another. The first longitudinal lumen 1306 is open to the outside of the handle threaded insert 1300 at the distal end 1301. The second longitudinal lumen 1308 is open to the outside of the handle threaded insert 1300 at the proximal end 1302. The slot 1320 opens to the first longitudinal lumen 1306.

Figure 14A:
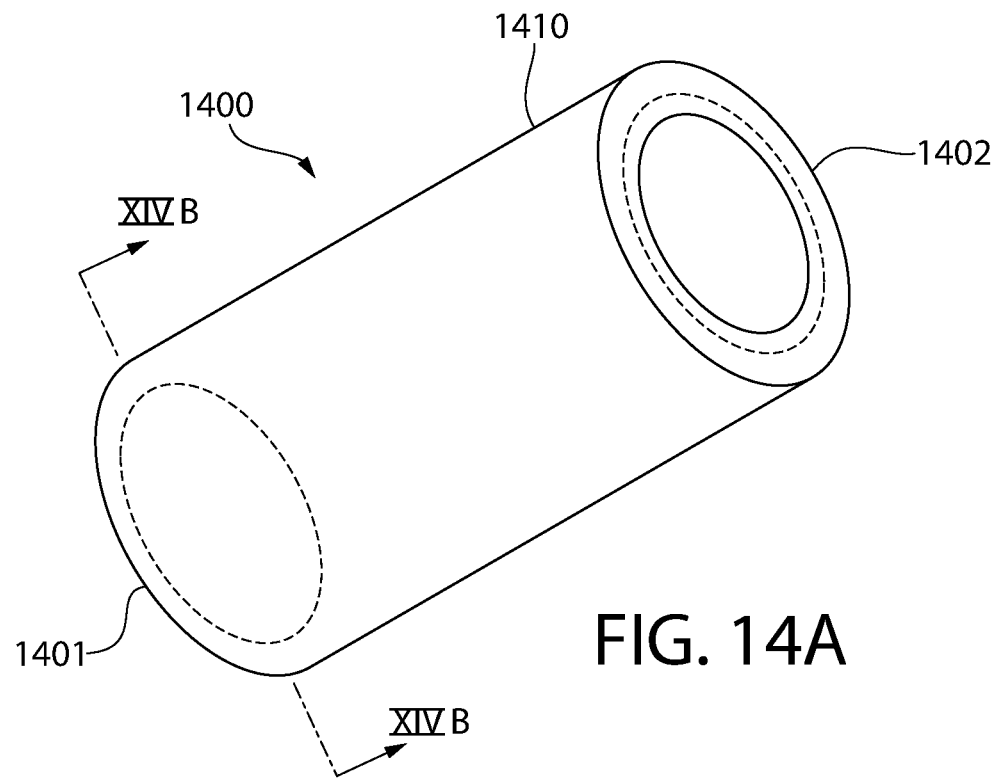
FIG. 14A is a perspective view of a seal housing of the transfemoral catheter of FIG. 1A, in accordance with an exemplary embodiment of the present invention.
Figure 14B:
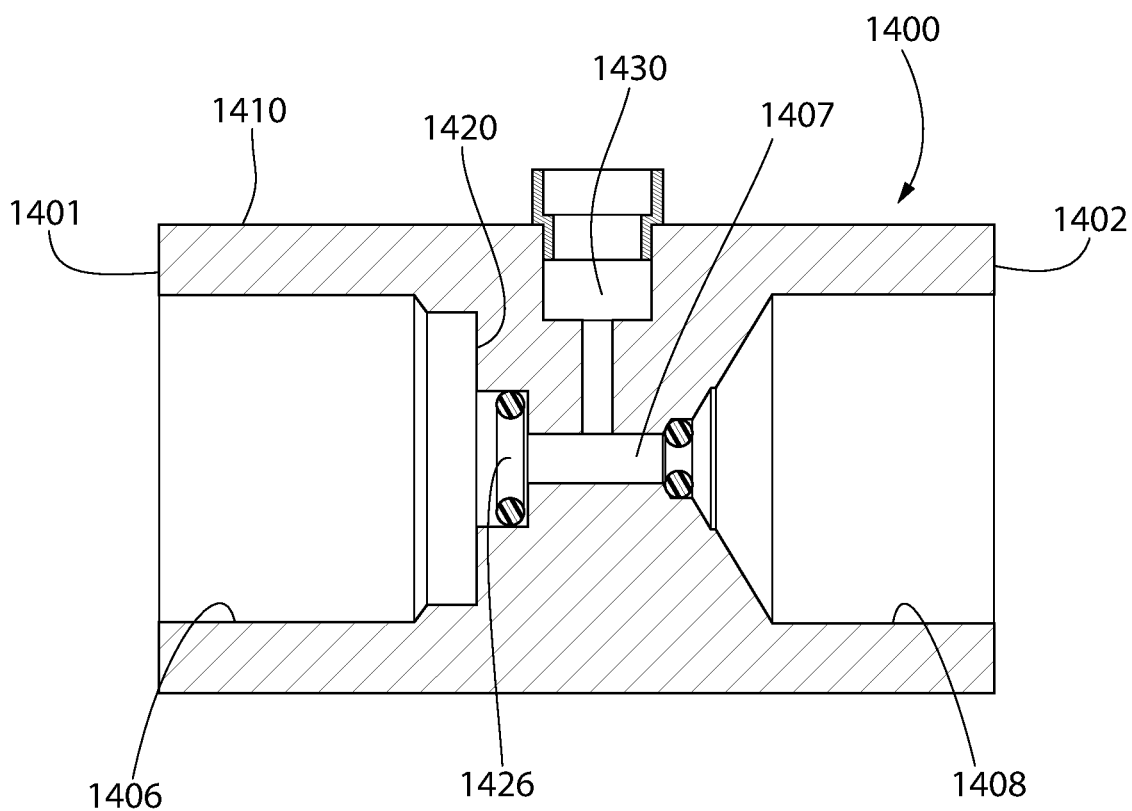
FIG. 14B is a cross-sectional view taken along line XIVB-XIVB of FIG. 14A, in accordance with an exemplary embodiment of the present invention.

A close-up, perspective view of the seal housing 1400 is illustrated in FIG. 14A. A cross-sectional view of the seal housing 1400 taken along line XIVB-XIVB of FIG. 14A illustrated in FIG. 14B. The seal housing 1400 comprises a distal end 1401, a proximal end 1402, and an outer wall 1410 extending from the distal end 1401 to the proximal end 1402. The outer wall 1410 has a generally cylindrical shape.

Disposed within the seal housing 1400 at the distal end 1401 is a first longitudinal lumen 1406. Disposed within the seal housing 1400 at the proximal end 1402 is a second longitudinal lumen 1408. The first and second longitudinal lumens 1406, 1408 communicate with one another through a central longitudinal lumen 1407. The first longitudinal lumen 1406 is open to the outside of the seal housing 1400 at the distal end 1401. The second longitudinal lumen 1408 is open to the outside of the seal housing 1400 at the proximal end 1402. The central longitudinal lumen 1407 has a narrower diameter than that of the lumens 1406 and 1408. Disposed at the end of the first longitudinal lumen 1406 adjacent to the lumen 1407 is an interior space 1426 comprising a stop surface 1420. A seal gland sits in interior space 1426. A metal ring sits in the section of the seal housing distally to the interior space 1426. The seal housing 1400 also includes a transverse opening 1430 that forms a passageway from the outer surface 1410 into the central longitudinal lumen 1407. The transverse opening 1430 provides a pathway for saline or other solution to flow into the lumen 246 for flushing and/or cleaning. The opening 1430 gives access to tube 240 for flushing the catheter. The opening 1430 also allows all inside lumens distal to 1426 to be flushed due to the laser cuts on the distal section of tube 240.

Figure 15A:
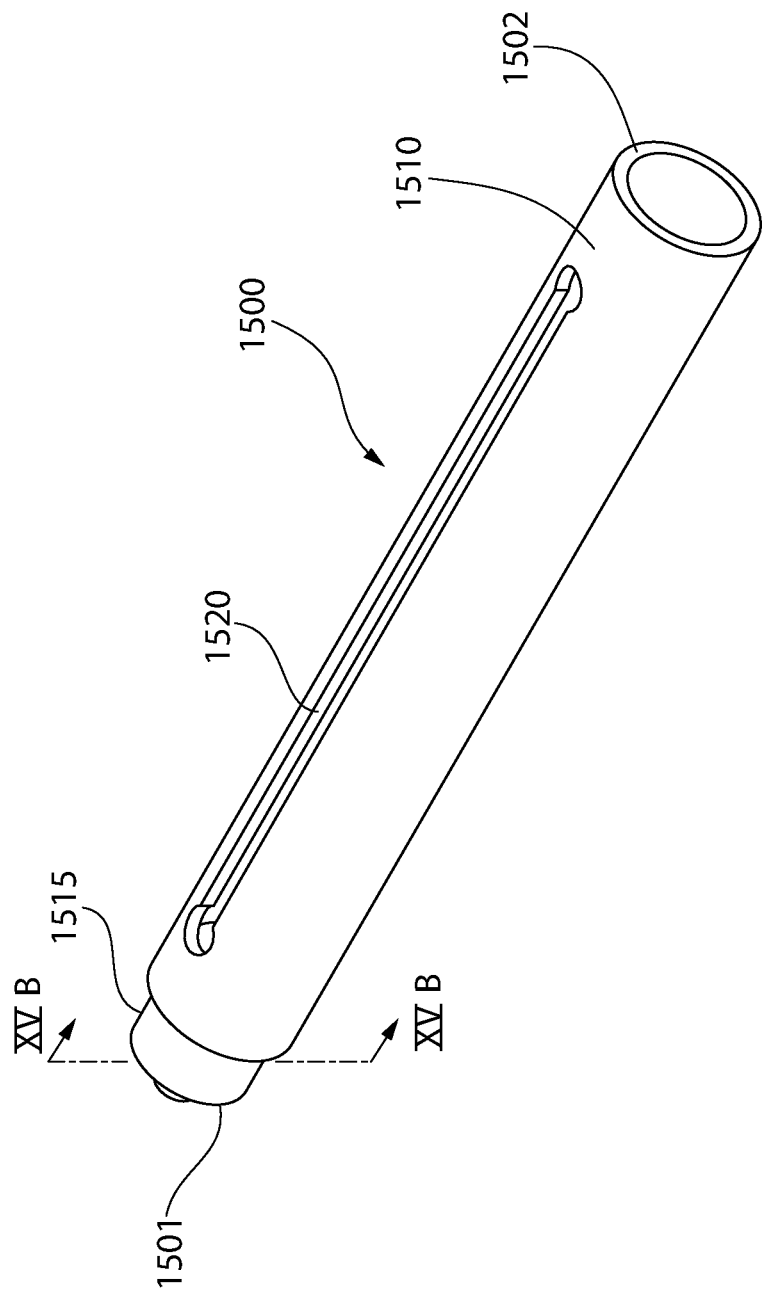
FIG. 15A is a perspective view of a proximal slider housing of the transfemoral catheter of FIG. 1A, in accordance with an exemplary embodiment of the present invention.

A close-up, perspective view of the proximal slider housing 1500 is illustrated in FIG. 15A. A cross-sectional view of the proximal slider housing 1500 taken along line XVB-XVB of FIG. 15A is illustrated in FIG. 15B. The proximal slider housing 1500 comprises a distal end 1501, a proximal end 1502, and an outer wall 1510 extending from the distal end 1501 to the proximal end 1502. The outer wall 1510 comprises a first section 1513, a second section 1515, and a third section 1517. The proximal slider housing 1500 further comprises a slot 1520 in the outer wall 1510.

The first section 1513 is disposed at the distal end 1501 and has a cylindrical shape. The second section 1515 is disposed proximally to the first section 1513 and has a cylindrical shape. The third section 1517 is disposed proximally to the second section 1515 and has a cylindrical shape. The third section 1517 extends to the proximal end 1502. The first section 1513 has a smaller diameter than the second section 1515, which has a smaller diameter than the third section 1517.

Disposed within the proximal slider housing 1500 in the first and second sections 1513 and 1515 and in a distal portion of the third section 1517 is a first longitudinal lumen 1506. Disposed within the proximal slider housing 1500 in the third section 1517 is a second longitudinal lumen 1508. The first and second longitudinal lumens 1506, 1508 communicate with one another. The first longitudinal lumen 1506 is open to the outside of the proximal slider housing 1500 at the distal end 1501. The second longitudinal lumen 1508 is open to the outside of the proximal slider housing 1500 at the proximal end 1502. The slot 1520 opens to the second longitudinal lumen 1508.

A cross-sectional view of a proximal slider 1600 is illustrated in FIG. 16. The proximal slider 1600 comprises a distal end 1601, a proximal end 1602, and an outer wall 1610 extending from the distal end 1601 to the proximal end 1602. The outer wall 1610 has a generally cylindrical shape.

Disposed within the proximal slider 1600 is a first longitudinal lumen 1606 extending from the distal end 1601 to a midpoint 1613 of the outer wall 1610. Also disposed within the proximal slider 1600 is a second longitudinal lumen 1608 extending from the midpoint 1613 of the outer wall 1610 to the proximal end 1602. The first and second longitudinal lumens 1606, 1608 communicate with one another. The first longitudinal lumen 1606 is open to the outside of the proximal slider 1600 at the distal end 1601. The second longitudinal lumen 1608 is open to the outside of the proximal slider 1600 at the proximal end 1602. The lumen 1606 has a narrower diameter than that of the lumen 1608.

Also disposed in the proximal slider 1600 is a transverse lumen 1620. The transverse lumen 1620 is disposed in the proximal slider 1600 perpendicularly to the lumen 1606. A screw 1630 is positioned within the transverse lumen 1620 and serves to secure the proximal slider 1600 within the proximal slider housing 1500. Specifically, the proximal slider 1600 is at least partially positioned within the proximal slider housing 1500 and is configured to move axially relative to the proximal slider housing 1500. The screw 1630 can be altered between a locked state that prevents the proximal slider 1600 from being able to move axially relative to the proximal slider housing 1500 and an unlocked state that permits the proximal slider 1600 to slide axially relative to the proximal slider housing 1500. Specifically, in the locked state the screw 1630 presses downwardly on the outer wall 1510 of the proximal slider housing 1500 to prevent the proximal slider 1600 from moving and when in the unlocked state the screw 1630 is no longer in contact with the outer wall 1510 of the proximal slider housing 1500, thereby allowing the proximal slider 1600 to move. This operation and its effect will be described in more detail below with particular reference to FIGS. 24A and 24B.

Figure 17A:
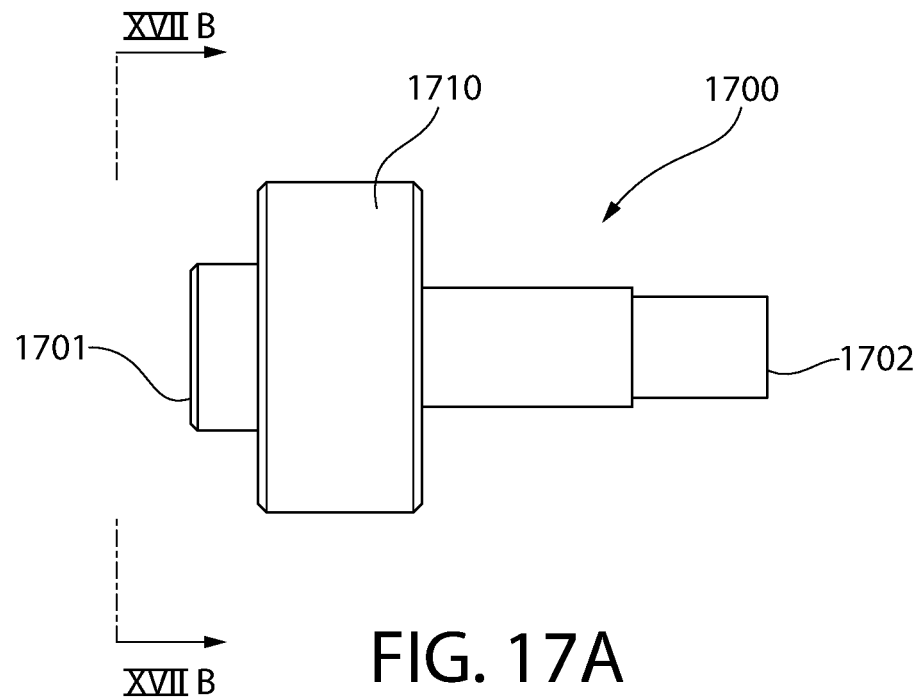
FIG. 17A is a side view of an inner ring of the transfemoral catheter of FIG. 1A, in accordance with an exemplary embodiment of the present invention.
Figure 17B:
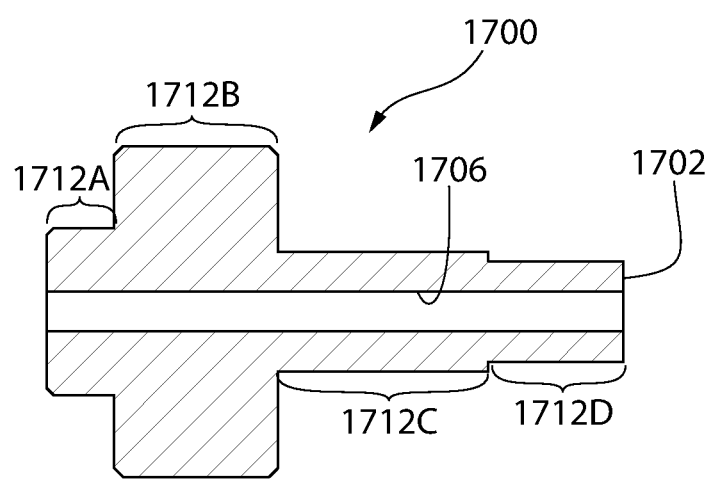
FIG. 17B is a cross-sectional view taken along line XVIIB-XVIIB of FIG. 17A, in accordance with an exemplary embodiment of the present invention.

A close-up, perspective view of the inner ring 1700 is illustrated in FIG. 17A. A cross-sectional view of the inner ring 1700 taken along line XVIIB-XVIIB of FIG. 17A is illustrated in FIG. 17B. The inner ring 1700 comprises a distal end 1701, a proximal end 1702, and an outer wall 1710 extending from the distal end 1701 to the proximal end 1702. The outer wall 1710 comprises four sections: a distal section 1712A, a mid-section 1712B, a first proximal section 1712C, and a second proximal section 1712D. The distal section 1712A has a smaller diameter than the mid-section 1712B. The first proximal section 1712C has a smaller diameter than the mid-section 1712B. The second proximal section 1712D has a smaller diameter than the first proximal section 1712C. Disposed within the inner ring 1700 is a longitudinal lumen 1706. The longitudinal lumen 1706 is open to the outside of the inner ring 1700 at the distal end 1701 and the proximal end 1702.

Figure 18A:
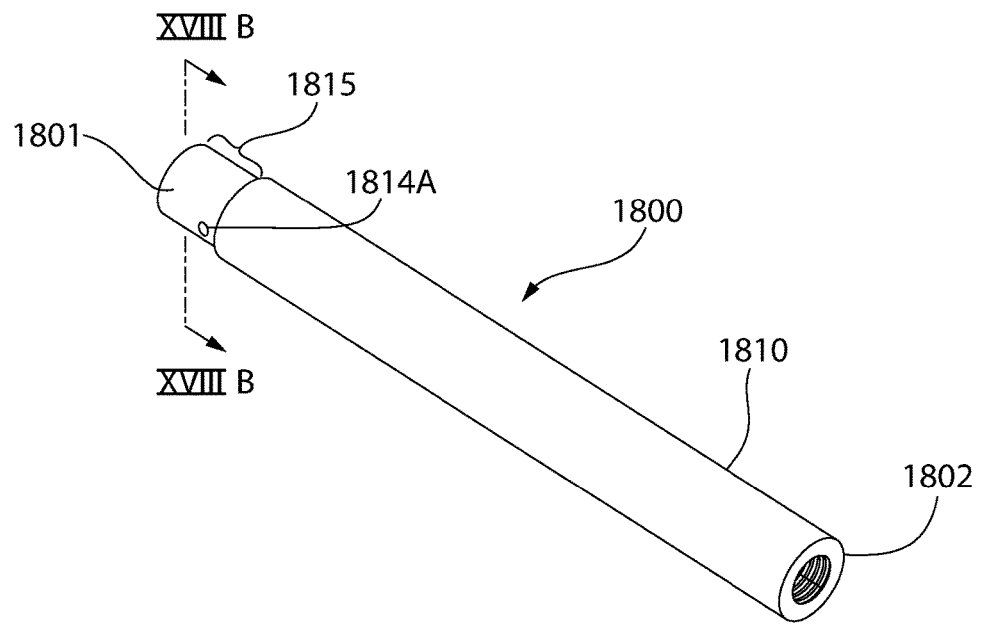
FIG. 18A is a perspective view of an outer handle of the transfemoral catheter of FIG. 1A, in accordance with an exemplary embodiment of the present invention.
Figure 18B:
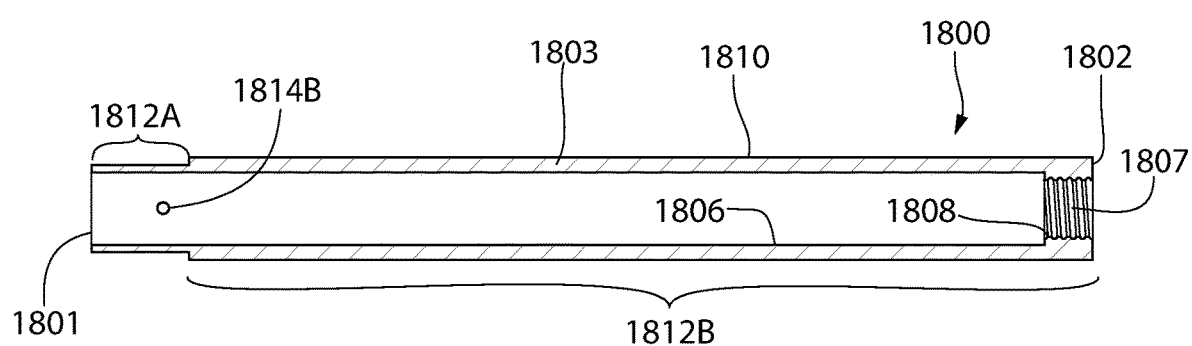
FIG. 18B is a cross-sectional view taken along line XVIIIB-XVIIIB of FIG. 18A, in accordance with an exemplary embodiment of the present invention.

A close-up, perspective view of the outer handle 1800 is illustrated in FIG. 18A. A cross-sectional view of the outer handle 1800 taken along line XVIIIB-XVIIIB of FIG. 18A is illustrated in FIG. 18B. The outer handle 1800 comprises a distal end 1801, a proximal end 1802, and an outer wall 1810 extending from the distal end 1801 to the proximal end 1802. The outer wall 1810 comprises a first section 1812A and a second section 1812B. The outer handle 1800 further comprises a pair of apertures 1814A and 1814B in the outer wall 1810.

The first section 1812A is disposed at the distal end 1801 and has a cylindrical shape. The second section 1812B is disposed proximally to the first section 1812A and extends from the first section 1812A to the proximal end 1802. The first section 1812A has a smaller diameter than the second section 1812B.

Disposed within the outer handle 1800 is a first longitudinal lumen 1806 and a second longitudinal lumen 1808. The first and second longitudinal lumens 1806, 1808 communicate with one another. The first longitudinal lumen 1806 is open to the outside of the outer handle 1800 at the distal end 1801. The second longitudinal lumen 1808 is open to the outside of the outer handle 1800 at the proximal end 1802. Disposed within the second longitudinal lumen 1808 are threads 1807. The outer handle 1800 is coupled to the handle threaded insert 1300 via the threads 1807 of the outer handle 1800 and the threaded section 1315 of the handle threaded insert 1300. Thus, the outer handle 1800 can move relative to the handle threaded insert 1300 by rotating the outer handle 1800 relative to the handle threaded insert 1300. The outer handle 1800 is operably coupled to the outer sheath 260 via the braided shaft 270 such that axial movement of the outer handle 1800, which is achieved by rotating the outer handle 1800 relative to the handle threaded insert 1300, causes the outer sheath 260 to move axially. This movement is what is used to expose and deploy the replacement aortic valve during operation, as described in more detail below.

Figure 19A:
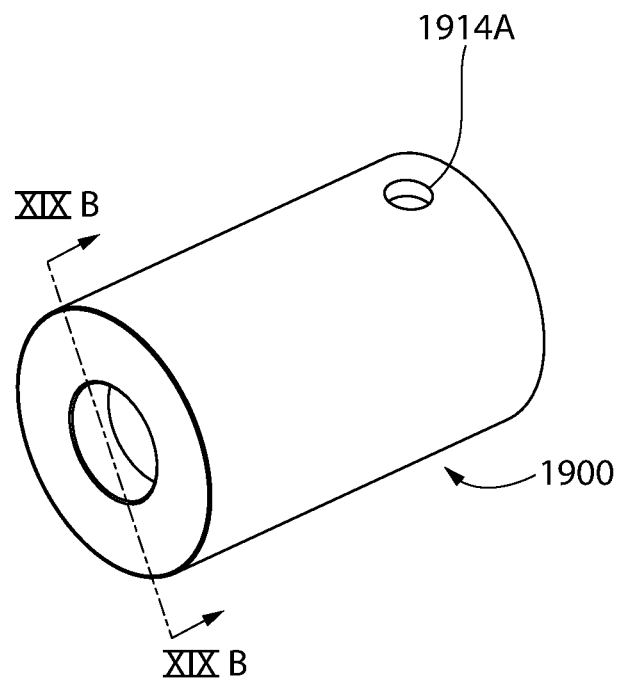
FIG. 19A is a perspective view of an outside cap of the transfemoral catheter of FIG. 1A, in accordance with an exemplary embodiment of the present invention.
Figure 19B:
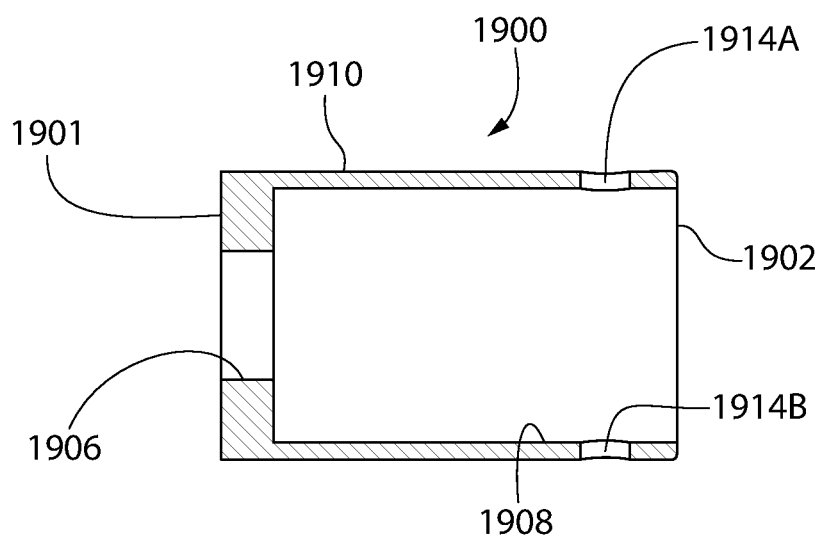
FIG. 19B is a cross-sectional view taken along line XIXB-XIXB of FIG. 19A, in accordance with an exemplary embodiment of the present invention.

A close-up, perspective view of an outside cap 1900 is illustrated in FIG. 19A. A cross-sectional view of the outside cap 1900 taken along line XIXB-XIXB of FIG. 19A is illustrated in FIG. 19B. The outside cap 1900 comprises a distal end 1901, a proximal end 1902, and an outer wall 1910 extending from the distal end 1901 to the proximal end 1902. The outside cap 1900 further comprises a pair of apertures 1914A and 1914B in the outer wall 1910. Set screws 1915 or the like are inserted into the apertures 1914A, 1914B to couple the outside cap 1900 to the outer handle 1800 (see FIG. 4). The outer wall 1910 has a cylindrical shape.

Disposed within the outside cap 1900 is a first longitudinal lumen 1906 and a second longitudinal lumen 1908. The first and second longitudinal lumens 1906, 1908 communicate with one another. The first longitudinal lumen 1906 is open to the outside of the outside cap 1900 at the distal end 1901. The second longitudinal lumen 1908 is open to the outside of the outside cap 1900 at the proximal end 1902. The diameter of the first longitudinal lumen 1906 is less than that of the second longitudinal lumen 1908.

Figure 20:
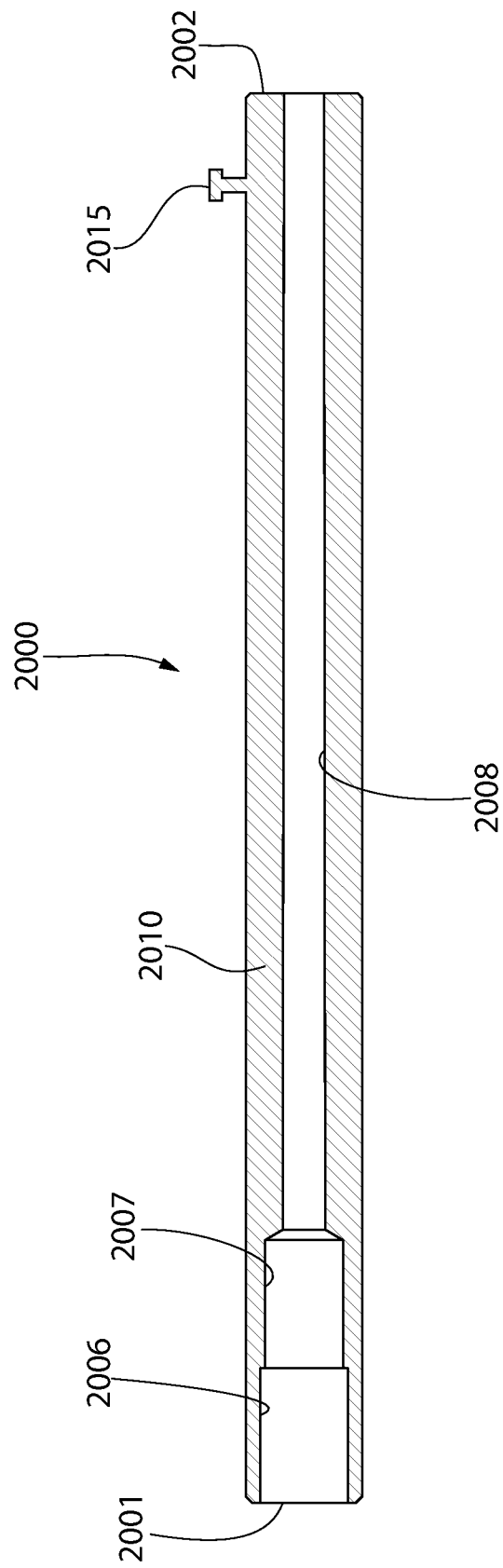
FIG. 20 is a cross-sectional view of a distal slider of the transfemoral catheter of FIG. 1A, in accordance with an exemplary embodiment of the present invention.

A cross-sectional view of the distal slider 2000 is illustrated in FIG. 20. The distal slider 2000 comprises a distal end 2001, a proximal end 2002, and an outer wall 2010 extending from the distal end 2001 to the proximal end 2002. The outer wall 2010 has a cylindrical shape.

Disposed within the distal slider 2000 at the distal end 2001 are a first longitudinal lumen 2006 and a second longitudinal lumen 2007. Also disposed within the distal slider 2000 is a third longitudinal lumen 2008 extending from the second longitudinal lumen 2007 proximally to the proximal end 2002. The first, second, and third longitudinal lumens 2006, 2007, 2008 communicate with one another. The first longitudinal lumen 2006 is open to the outside of the distal slider 2000 at the distal end 2001. The third longitudinal lumen 2008 is open to the outside of the distal slider 2000 at the proximal end 2002. The distal slider 2000 is housed within the outer handle 1800. Furthermore, a proximal portion of the distal slider 2000 is disposed within the distal end of the handle threaded insert 1300 and a proximal portion of the inner ring 1700 is disposed within a distal portion of the distal slider 2000. The distal slider 2000 is slidable relative to and within the first longitudinal lumen 1306 of the handle threaded insert 1300. Specifically, rotation of the outer handle 1800 relative to the handle threaded insert 1300 causes the outer handle 1800, outside cap 1900, inner ring 1700, and distal slider 2000 to move axially in the proximal direction, as described in more detail below.

Referring again to FIGS. 4 and 13A through 20, the relationship of the various components of the handle assembly 400 will be discussed in greater detail. The proximal end 1402 of the seal housing 1400 is connected to the distal end 1501 of the proximal slider housing 1500 to form a proximal slider assembly 420. Specifically, the first and second sections 1513, 1515 of the outer wall 1510 of the proximal slider housing 1500 are disposed within the second longitudinal lumen 1408 of the seal housing 1400. The distal outer wall of the proximal slider housing 1500 is secured to the proximal inner wall of the seal housing 1400 by way of threads. The proximal slider housing 1500 screws into the seal housing 1400 and may be held in place by a set screw. In other embodiments, the second section 1515 of the outer wall 1510 may be bonded, such as by a solvent bond, or adhered to the second longitudinal lumen 1408 of the seal housing 1400.

The distal end 1401 of the seal housing 1400 is connected to the proximal end 1302 of the handle threaded insert 1300.

Specifically, the second smooth section 1312 of the outer wall 1310 of the handle threaded insert 1300 is disposed within the first longitudinal lumen 1406 of the seal housing 1400. In an exemplary embodiment, the second smooth section 1312 of the outer wall 1310 of the handle threaded insert 1300 is bonded, such as by an adhesive. In another exemplified embodiment, the proximal end 1302 of the handle threaded insert 1300 is secured to the distal lumen of the seal housing 1400 by way of threads. In such embodiment, the threaded handle may screw into the seal housing 1400 and a set screw may be placed to help anchor the pieces together. In another exemplary embodiment, the second section 1312 of the outer wall 1310 of the handle threaded insert 1300 comprises threads disposed thereon, which threads complement threads disposed in the first longitudinal lumen 1406 of the seal housing 1400. In such embodiment, the seal housing 1400 is threaded onto the second section 1312 of the outer wall 1310 of the handle threaded insert 1300.

The proximal end 1702 of the inner ring 1700 is connected to the distal end 2001 of the distal slider 2000. Specifically, the first proximal section 1712C and the second proximal section 1712D of the outer wall 1710 of the inner ring 1700 are disposed within the first and second longitudinal lumens 2006, 2007 of the distal slider 2000. In an exemplary embodiment, the first proximal section 1712C and the second proximal section 1712D of the outer wall 1710 of the inner ring 1700 are bonded, such as via a solvent bond, or otherwise adhered within the first and second longitudinal lumens 2006, 2007 of the distal slider 2000. The first and second proximal sections 1712C and 1712D are disposed within the within the first and second longitudinal lumens 2006 and 2007, respectively. They are adhered via threads on the first proximal section 1712C which screws into complimentary threads into the first longitudinal lumen 2006 only. In the exemplified embodiment, there are no solvent bonds, although solvent bonds may be used in alternative embodiments.

The combined inner ring 1700 and distal slider 2000 (also referred to as a distal slider assembly 410) are disposed within the distal end 1801 of the outer handle 1800. Specifically, the first proximal section 1712C and the second proximal section 1712D of the outer wall 1710 of the inner ring 1700 and all of the distal slider 2000 are disposed in the lumen 1806 between the distal end 1801 and about a midpoint 1803 of the outer handle 1800. The distal section 1712A and the mid-section 1712B of the outer wall 1710 of the inner ring 1700 are disposed outside the outer handle 1800. The mid-section 1712B abuts the distal end 1801 of the outer handle 1800 and is held in place by the outside cap 1900.

As illustrated above and best depicted in FIG. 4, the screws 1915 may be passed through the apertures 1914A and 1914B in the outer wall 1910 of the outside cap 1900 into corresponding apertures 1814A and 1814B in the outer wall 1810 of the outer handle 1800. The screws 1915 are used to secure the outside cap 1900 to the outer handle 1800, thereby retaining the distal slider assembly 410 against and in the outer handle 1800 to prevent axial movement of the distal slider assembly 410 relative to the outer handle 1800. This also facilitates the proximal movement of the distal slider assembly 410 when the outer handle 1800 is moved proximally.

The handle threaded insert 1300 is disposed within the lumen 1806 of the outer handle 1800. Specifically, the first smooth section 1311 of the outer wall 1310 of the threaded insert 1300 is disposed within the lumen 1806 of the outer handle 1800. The threaded section 1315 of the threaded insert 1300 is disposed within and engaging the threads 1807 of the second longitudinal lumen 1808 of the outer handle 1800. As can be seen in FIG. 4, the threaded section 1315 at about the mid-section 1313 engages the threads 1807 of the second longitudinal lumen 1808 of the outer handle 1800.

The proximal end 2002 of the distal slider 2000 is disposed within the lumen 1306 of the handle threaded insert 1300 at the distal end 1301 of the handle threaded insert 1300. When so positioned, the handle threaded insert 1300 does not move and radial movement of the distal slider 2000 is prevented by a screw pin 2015 (FIG. 20) that extends through the slot 1320 in the first smooth section 1311 of the handle threaded insert 1300. Since the handle threaded insert 1300 does not move at all, the pin 2015 prevents rotational movement of the distal slider 2000, but allows the distal slider 2000 to move axially.

The proximal end 243 of the second tube 240 is terminated by a ring 430 disposed at the proximal end 1302 of the threaded insert 1300. The ring 430 prevents the proximal end of the second tube 240 from being pushed into the threaded insert 1300 as it abuts the proximal end 1302 of the threaded insert 1300. The ring 430 may also prevent the second tube 240 from being pushed through the seal housing 1400 and into the proximal slider assembly 420 during deployment, as described in more detail below. The ring 430 experiences compressive forces. Thus, the ring 430 limits movement of the proximal end of the second tube 240 relative to the threaded insert 1300.

A distal end 421 of the proximal slider assembly 420 is attached to the proximal end 1302 of the handle threaded insert 1300. So disposed, the ring 430 is disposed within the interior space 1426 of the seal housing 1400 or in the space between the first longitudinal lumen 1406 and the interior space 1426. The stop surface 1420 of the interior space 1426 prevents the proximal end of the second tube 240 from moving proximally through the proximal slider assembly 420. Thus, the ring 430 limits movement of the proximal end of the second tube 240 relative to the proximal slider assembly 420.

The second tube 240 is held in place because the ring 430 is corralled between the proximal slider assembly 420 and the handle threaded insert 1300. When the outer handle 1800 is rotated counter-clockwise relative to the handle threaded insert 1300, the braided shaft 270 is pulled axially proximally and when the outer handle 1800 is rotated clockwise relative to the handle threaded insert, the braided shaft 270 and the outer sheath 260 are moved axially distally. The second tube 240 is not advanced or moved during the rotation of the outer handle 1800.

"Clockwise" is used herein to describe the rotation of the outer handle 1800 in a clockwise direction when viewed from the proximal end 102 of the transfemoral catheter 100. "Counterclockwise" is used herein to describe the rotation of the outer handle 1800 in a counterclockwise direction when viewed from the proximal end 102 of the transfemoral catheter 100). Of course, although clockwise rotation of the outer handle 1800 is described as causing distal movement and counterclockwise rotation of the outer handle 1800 is described as causing proximal movement, the opposite could be true by modifying the slant of the threads on the outer handle 1800 and the handle threaded insert 1300. The terms "clockwise" and "counterclockwise" could be replaced with "first rotational direction" and "second rotational direction" in some embodiments.

Briefly, as the outer handle 1800 is turned in a counter-clockwise direction, the threads 1808, which engage the threaded portion 1315 of the handle threaded insert 1300, move the outer handle 1800 proximally axially, taking with it the distal slider assembly 410. As the outer handle 1800 continues to be rotated counterclockwise, it moves the distal slider assembly 410 proximally, which in turn moves the braided shaft 270 and the outer sheath 260 proximally in the axial direction. If the outer handle 1800 is rotated a sufficient number of times in the counterclockwise direction, the outer handle 1800 will move further and further proximally in the axial direction, and eventually it will expose the expandable wall assembly 220 due to the proximal movement of the outer sheath 260. To be clear, in the exemplified embodiment the expandable wall assembly 220 does not move during rotation of the outer handle 1800, but the expandable wall assembly 220 becomes exposed due to the movement of the components and structures that surround the expandable wall assembly 220. The distal slider assembly 410 is prevented from rotating relative to the threaded insert 1300 by way of the pin 2015 disposed on the distal slider 2000. The pin 2015 engages with the slot 1320 of the threaded insert 1300 to prevent rotation of the distal slider assembly 410 relative to the threaded insert 1300. Because the distal slider 2000 cannot move radially/rotationally, the inner ring 1700 cannot move radially/rotationally (rather, it moves only axially). Since the inner ring 1700 cannot move radially/rotationally, the braided shaft 270 and the outer sheath 260 cannot move radially/rotationally. In the exemplified embodiment, rotation of the outer handle 1800 in the counterclockwise direction causes movement of the foregoing components axially in the proximal direction and rotation of the outer handle 1800 in the clockwise direction causes movement of the foregoing components axially in the distal direction.

The proximal end 232 of the first tube 230 is secured within the second longitudinal lumen 1608 of the proximal slider 1600. In an exemplary embodiment, the second longitudinal lumen 1608 is filled with an epoxy resin to secure the proximal end 232 of the first tube 230 therein. Thus, translation of the proximal slider 1600 causes translation of the first tube 230.

As described above, the proximal slider 1600 comprises a transverse lumen 1620. A screw 1630 is disposed through the slot 1520 of the proximal slider housing 1500 and into the transverse lumen 1620. When tightened, the screw 1630 secures the proximal slider 1600 within the proximal slider housing 1500.

When the screw 1630 is loosened to unsecure the proximal slider 1600 from the proximal slider housing 1500, the first tube 230 may be moved independently of the second tube 240 by moving the proximal slider 1600. The distal end 231 of the first tube 230 and the expandable wall 900 are coupled to the distal end 801 of the insert 800. More specifically, in some embodiments the expandable wall 900 mates with the proximal section of the threaded insert 800 and the first tube 230 mates with the inner lumen 806" of the threaded insert 800. When the screw 1630 is loosened, the screw 1630 can be pulled proximally (or distally) by way of the slot 1520 in the proximal slider housing 1500. Sliding this screw 1630 proximally slides the proximal slider 1600 and the first tube 230 along with it. This causes the first tube 230 to move proximally inside the lumen of the second tube 240 (which remains stationary), which causes the proximal movement of the insert 800, which causes the axial compression of the expandable wall 900

Thus, movement of the first tube 230 proximally relative to the second tube 240 causes the expandable wall 900 to compress axially and expand radially (i.e., alter from its structure shown in FIG. 9A to its structure shown in FIG. 9B). After the expandable wall 900 is axially compressed to a desired amount, the screw 1630 may be again tightened to secure the proximal slider 1600 within the proximal slider housing 1500. Thus, the handle assembly 400 provides for axial movement or translation of the first tube 230 relative to the second tube 240 when the screw 1630 is loosened so that it does not secure the proximal slider 1600 within the proximal slider housing 1500. Stated another way, loosening the screw 1630 allows the first tube 230 to move proximally to axially compress/radially expand the expandable wall 900. Tightening the screw 1630 allows to maintain the position of the first tube 230 so that the expandable wall 900 can be maintained in the axially compressed/radially expanded state until the valve is deployed.

Referring now to FIGS. 21A-28B, there are illustrated various steps of a method for implanting a transcatheter aortic valve (TAV) 2200, such as any of those described in U.S. Pat. No. 8,992,599 issued Mar. 31, 2015 having the same assignee as that of the present application, which patent is incorporated herein by this reference, using the transfemoral catheter 100, in accordance with an exemplary embodiment of the present invention. Prior to the method being performed, the aortic valve 2200 is loaded into the transfemoral catheter 100 by placing it over the second tube 240 between the expandable wall assembly 220 and the pusher 250. To do this, the TAV 2200 must be radially compressed so that it can fit within the outer sheath 260. Thus, the aortic valve 2200 may be placed within a radial compression tool, compressed, and then inserted into the outer sheath 260 between the expandable wall 900 and the pusher 250.

Figure 21B:
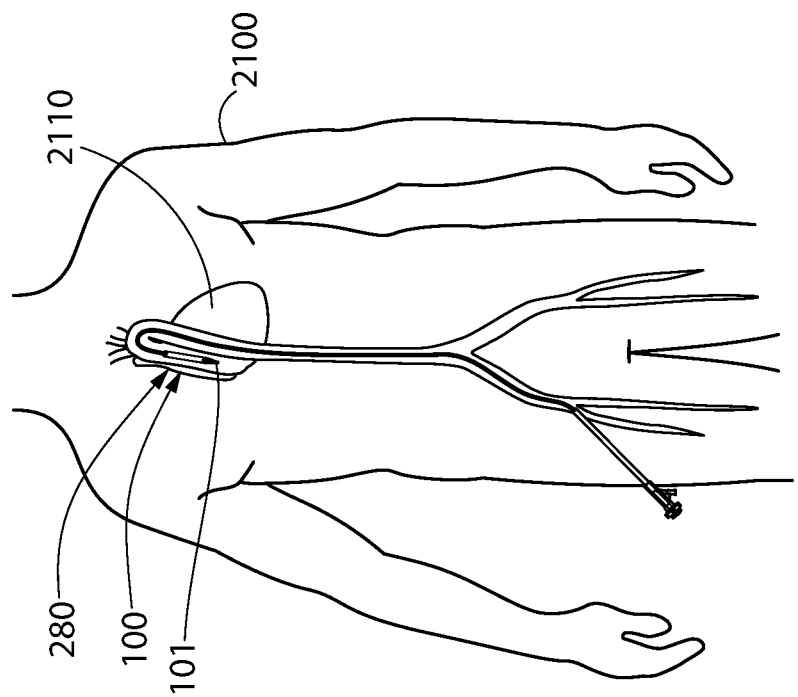
FIGS. 21A and 21B illustrate the manner in which the transfemoral catheter of FIG. 1A is inserted into a patient's body.
Figure 21A:
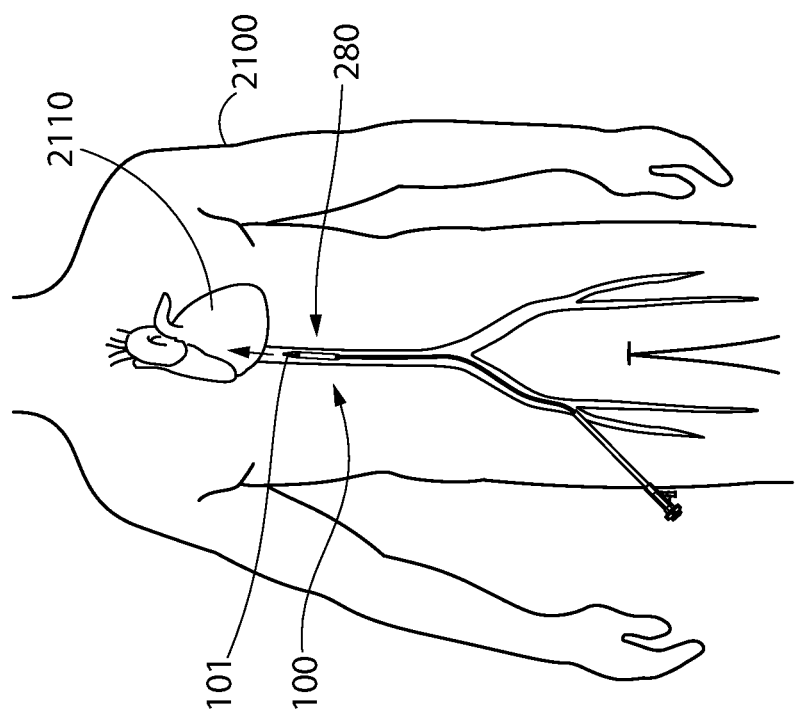

Referring first to FIGS. 21A and 21B, the first step in an aortic valve replacement procedure using the transfemoral catheter 100 and the TAV 2200 is to position a distal placement assembly 280 of the transfemoral catheter 100 in the proper position within the patient's heart 2110 so that when the TAV 2200 is deployed, it is located in the patient's aortic annulus. In some embodiments, the distal placement assembly 280 of the transfemoral catheter 100 may comprise the overmolded tip (or nosecone assembly) 600, the insert 700, the outer sheath 260 which houses the expandable wall assembly 220 and the pusher 250, as well as the braided shaft 270, which house the first and second tubes 230 and 240. Specifically, the distal end 101 of the transfemoral catheter 100 is inserted into the groin of a patient 2100 and moved distally into the heart 2110 of the patient 2100. The surgeon places the distal end 101 of the transfemoral catheter 100 so that the TAV 2200 is located within a diseased aortic valve 2115 (FIG. 21B) in the heart 2110 of the patient 2100. Fluoroscopy may be used to position the distal tip 101 of the transfemoral catheter 100 in a desired location.

Figure 22A:
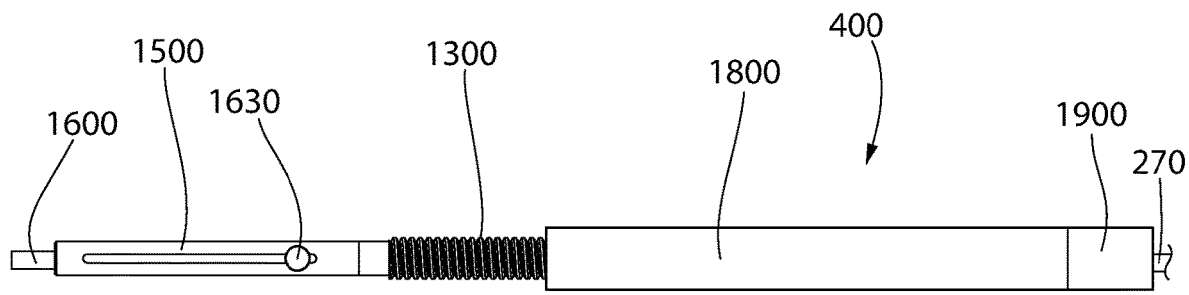
FIGS. 22A-29B illustrate the process of inserting a replacement aortic valve into a patient using the transfemoral catheter of FIG. 1A, wherein the "A" figures illustrate the operation of the handle assembly and the "B" figures illustrate the movement of the distal tip assembly responsive to the operation of the handle assembly, in accordance with an exemplary embodiment of the present invention.
Figure 22B:
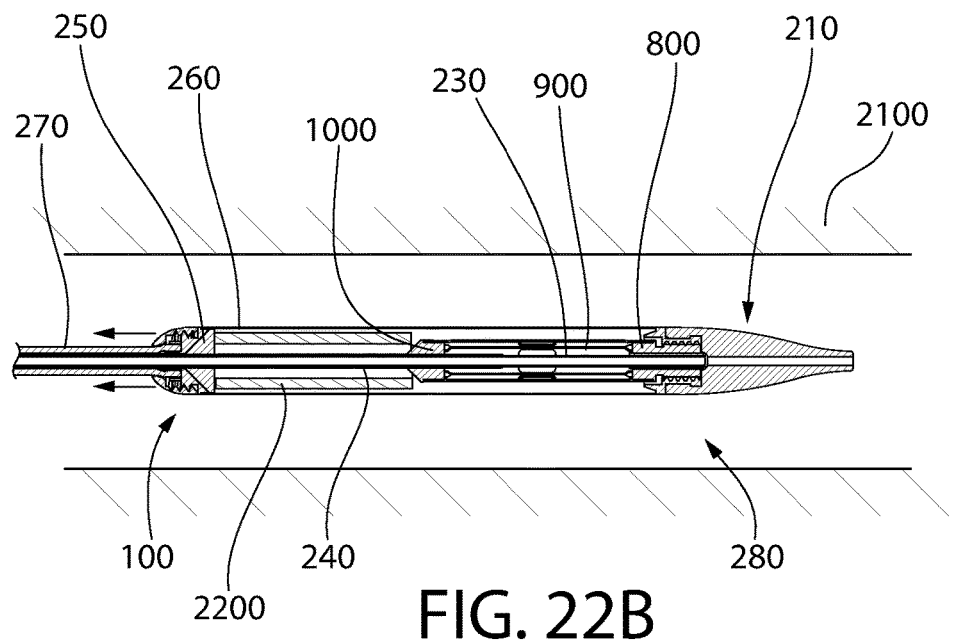

FIG. 22A illustrates the handle assembly 400 immediately after the distal tip 101 of the transfemoral catheter 100 has been placed in the desired location. FIG. 22B illustrates the distal placement assembly 280 in its desired position within the heart 2110 immediately after it has been placed in the desired location and prior to taking any next steps. As shown, at this point in the procedure the TAV 2200 remains housed within the outer sheath 260 between the expandable wall 900 and the pusher 250. As shown in FIG. 22B, the next step is to achieve axial movement of the outer sheath 260 in the proximal direction, which is right-to-left on the page as shown.

Figure 23A:
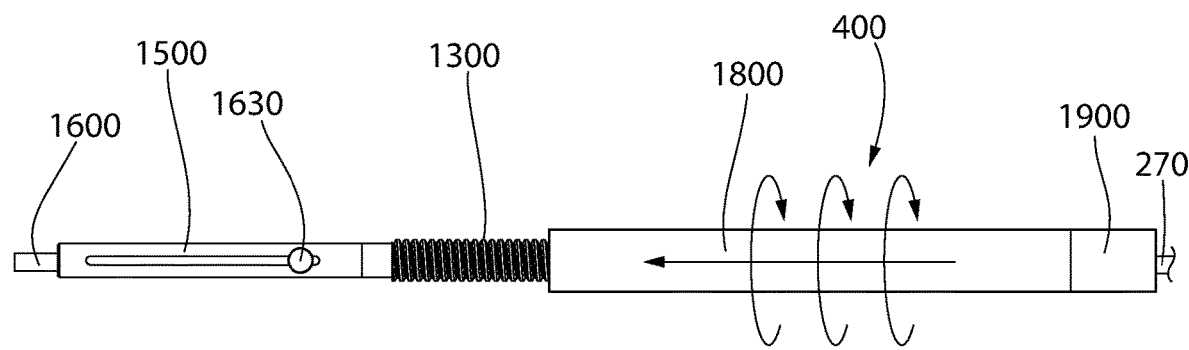
Figure 23B:
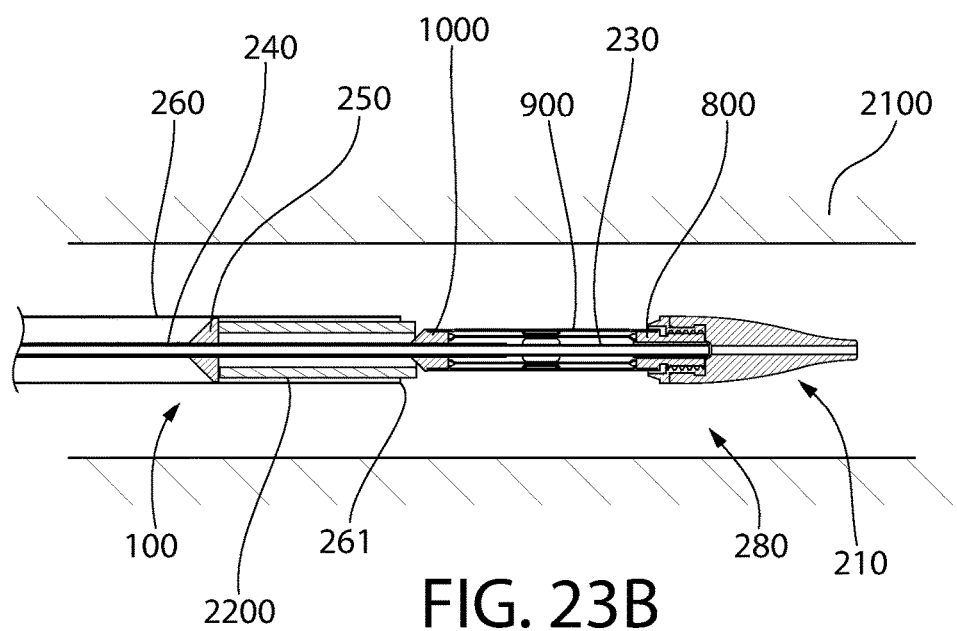

In that regard, referring to FIG. 23A, after positioning the distal end 101 of the transfemoral catheter 100 in the desired location within the heart 2110, the surgeon rotates the outer handle 1800 counterclockwise. Rotating the outer handle 1800 counterclockwise moves the outer handle 1800 axially in the proximal direction (i.e., away from the distal tip 210 or away from the nosecone/overmolded tip 600), which in turn moves the outside cap 1900, the inner ring 1700, the distal slider 2000, the braided shaft 270, and the outer sheath 260 axially in the proximal direction. During this step, the outer handle 1800 is rotated in the counterclockwise direction until the outer sheath 260 moves axially in the proximal direction a sufficient amount to expose the entirety of the expandable wall 900, as shown in FIG. 23B. In FIG. 23B, a portion of the TAV 2200 is also exposed or extending out of the distal end 261 of the outer sheath 260, but this is not required in all embodiments.

Figure 24A:
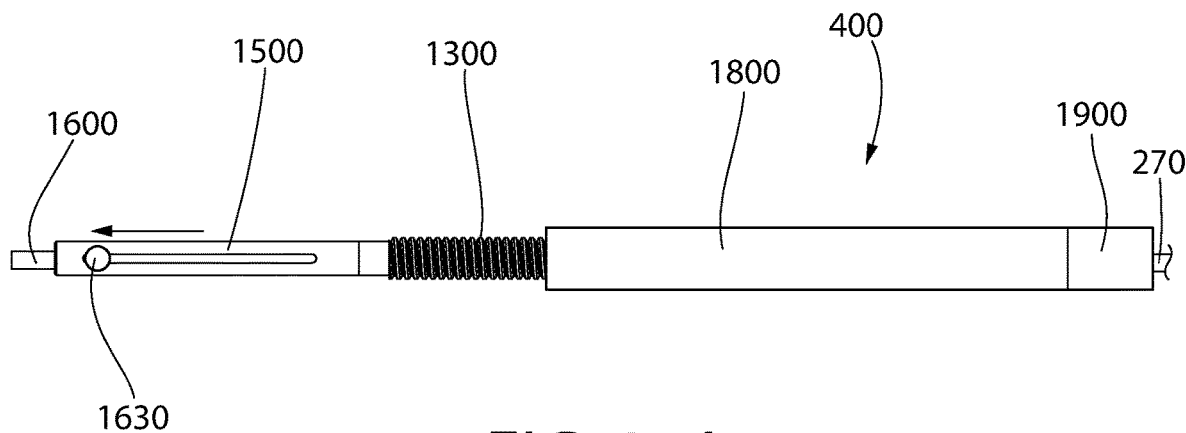
Figure 24B:
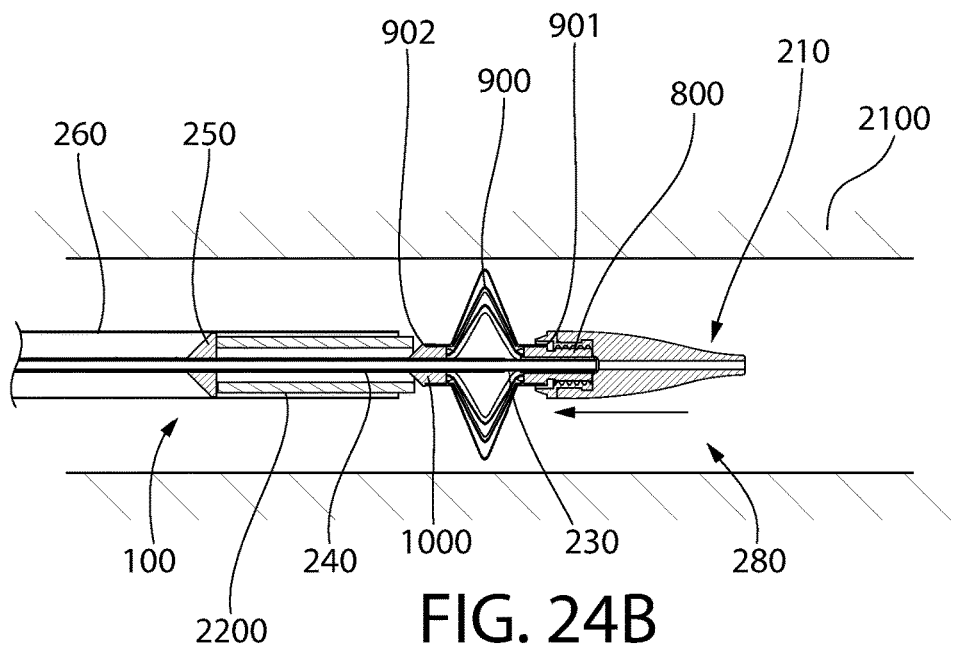

Referring to FIGS. 24A and 24B, the surgeon then loosens the screw 1630 and pulls the proximal slider 1600 proximally relative to the proximal slider housing 1500. This causes the first tube 230 to move proximally relative to the second tube 240, which causes the distal tip 210 and the distal end of the expandable wall 900 to move proximally. This movement of the proximal slider 1600 thereby causes the expandable wall 900 to axially compress and radially expand, as depicted in FIG. 24B. Specifically, the proximal end 902 of the expandable wall 900 remains in a fixed position and the distal end 901 of the expandable wall 900 moves axially in the proximal direction, thereby creating the axial compression and radial expansion of the expandable wall 900 that has been described herein. The surgeon then tightens the screw 1630 to lock the proximal slider 1600 into position within the proximal slider housing 1500, which also locks the expandable wall 900 in the axially compressed/radially expanded state.

It should be noted that axially compressing and radially expanding the expandable wall 900 as shown is desired, and perhaps even necessary, to prevent the TAV 2200 from becoming a projectile once it is fully removed from the outer sheath 260. Specifically, the TAV 2200 may be formed of a material that permits it to be radially compressed, but that is constantly working to expand back out to its original shape. Thus, as the outer sheath 260 continues to be pulled back to expose the TAV 2200, eventually a sufficient amount of the TAV 2200 will be exposed such that without the expandable wall 900 in position as shown, the replacement aortic valve 2200 may shoot out of the outer sheath 260. This is not desired because the TAV 2200 is already in its final desired position and thus no additional movement of the TAV 2200 is desired. Thus, the expandable wall 900 is radially expanded as shown so that the TAV 2200 cannot move axially past the expandable wall 900. Thus, the expandable wall 900 in the radially expanded state forms a stopper for the TAV 2200.

Figure 25A:
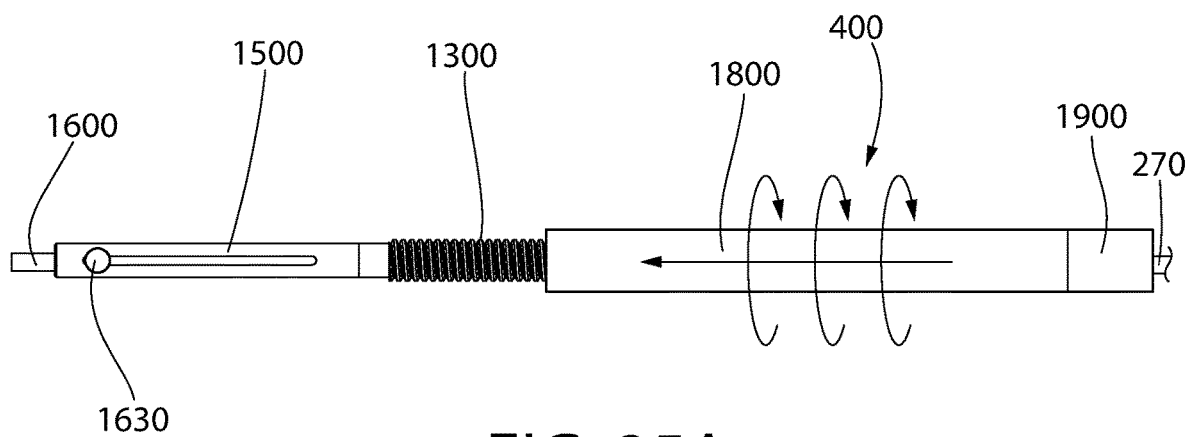
Figure 25B:
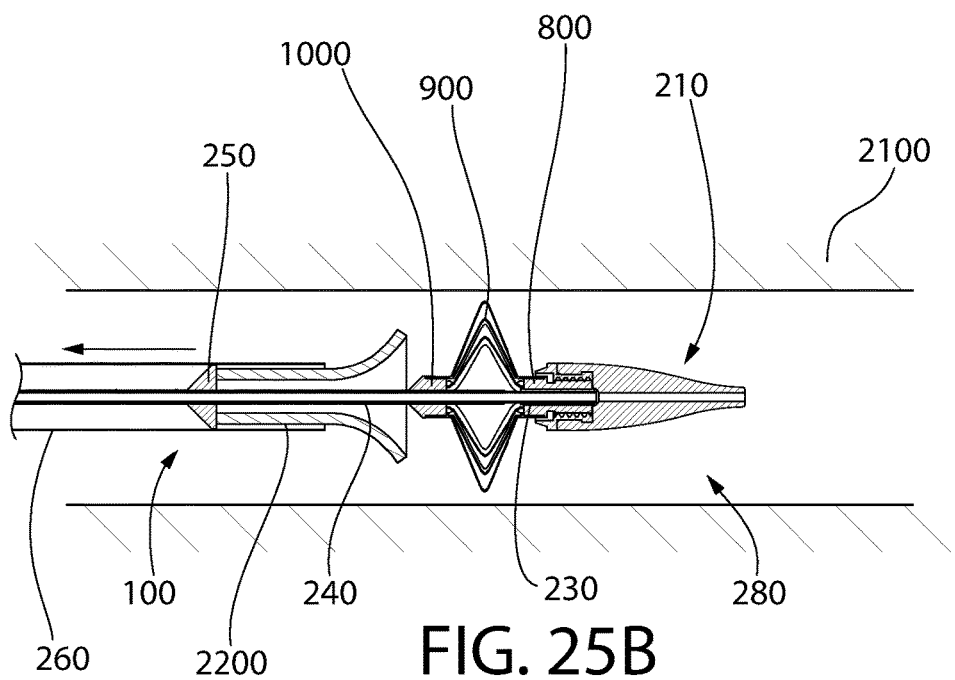

Referring to FIGS. 25A and 25B, next the surgeon may check the placement of the distal end 101 of the transfemoral catheter 100 using fluoroscopy to make sure everything remains in the desired location within the heart 2110. If everything remains in the proper position, the surgeon then continues to rotate the outer handle 1800 in the counterclockwise direction, which will move the outer sheath 260 in the proximal direction.

Figure 26A:
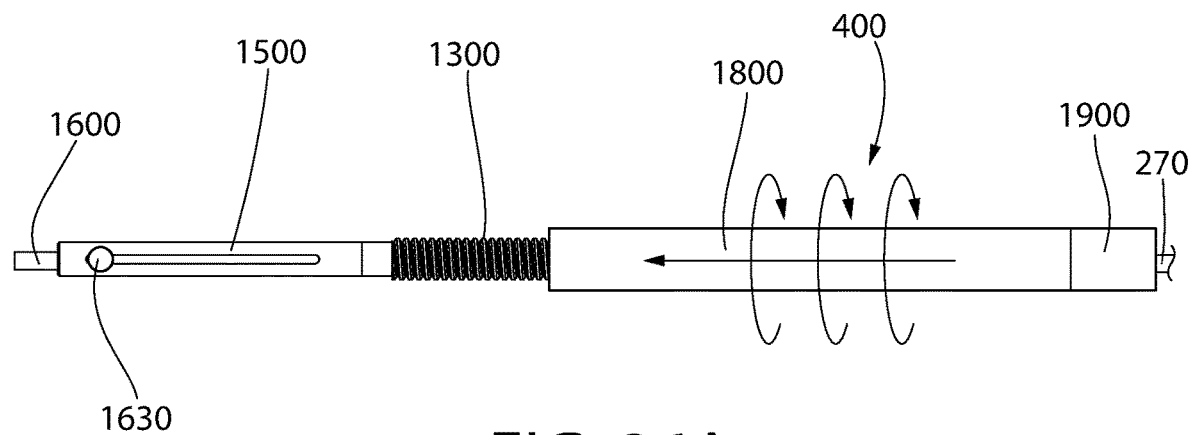
Figure 26B:
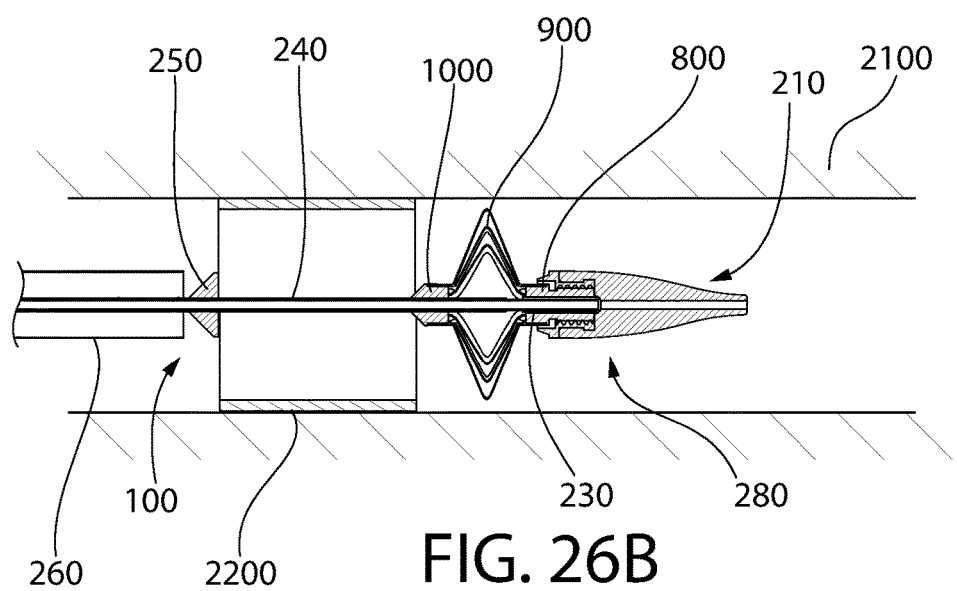

Referring to FIGS. 26A and 26B, the surgeon is still rotating the outer handle 1800 in the counterclockwise direction until the outer sheath 260 has moved axially in the proximal direction a sufficient distance so that the entirety of the TAV 2200 is external to the outer sheath 260. Specifically, the outer sheath 260 is moved axially in the proximal direction and the TAV 2200 remains in a fixed position such that eventually none of the TAV 2200 remains located in the outer sheath 260. During these steps shown in FIGS. 25A-26B, the expandable wall 900 remains in the axially compressed and radially expanded state so that as the TAV 2200 exists the outer sheath 260, the expandable wall 900 prevents the TAV 2200 from moving axially in the distal direction, as mentioned above. In FIG. 26B, the TAV 2200 is in its proper place within the heart 2110 of the patient 2100. The TAV 2200 has expanded radially into its biased state as discussed briefly above.

Figure 27A:
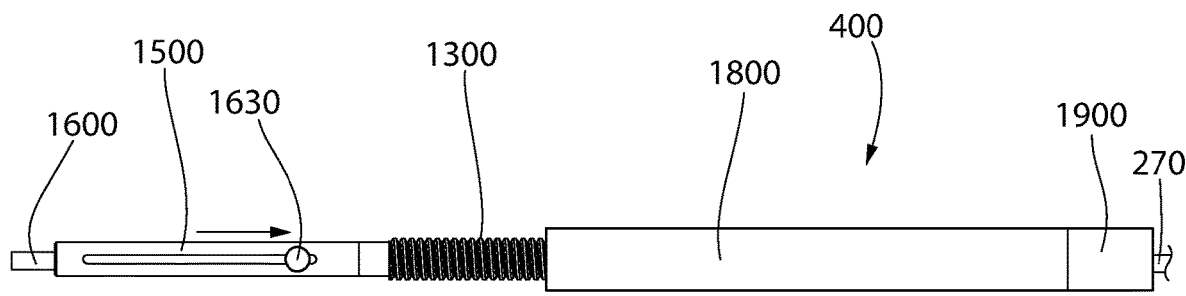
Figure 27B:
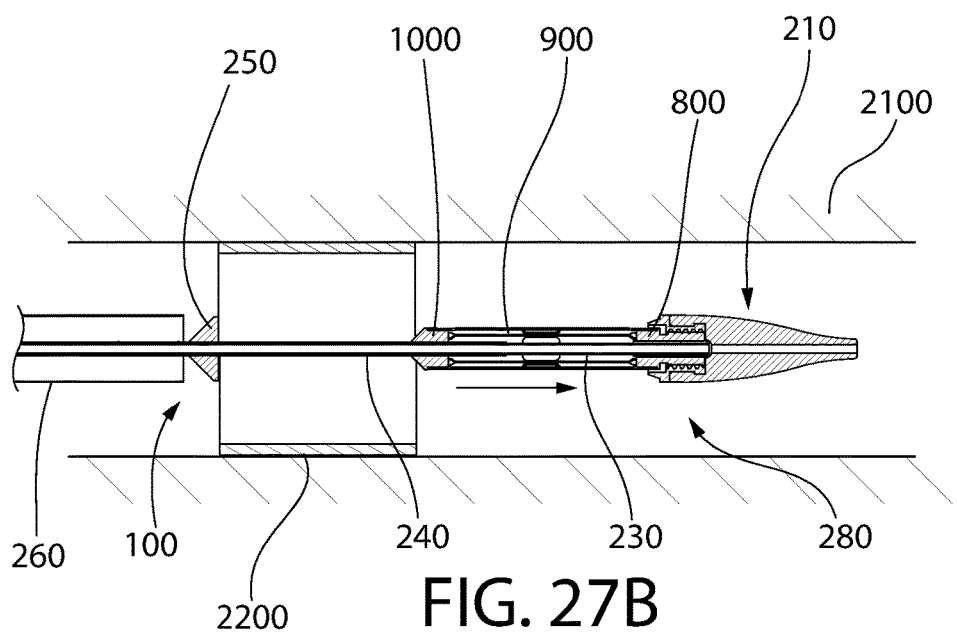

Next, referring to FIGS. 27A and 27B, the surgeon takes the necessary steps to remove the transfemoral catheter 100 from the patient's body while leaving the TAV 2200 in place. Thus, the surgeon loosens the screw 1630 and pushes the proximal slider 1600 distally. This causes the first tube 230 to move distally relative to the second tube 240, thereby causing the expandable wall 900 to straighten (i.e., expand axially and compress radially). As a result, the expandable wall 900 is now of a proper diameter so that it can fit back into the outer sheath 260. The surgeon may then tighten the screw 1630 to lock the expandable wall 900 in the straight position if so desired, although this may not be required in all embodiments.

Figure 28A:
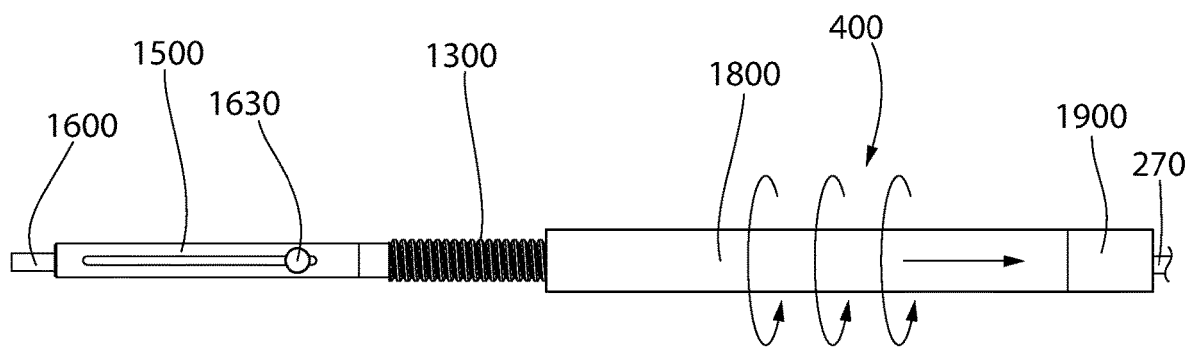
Figure 28B:
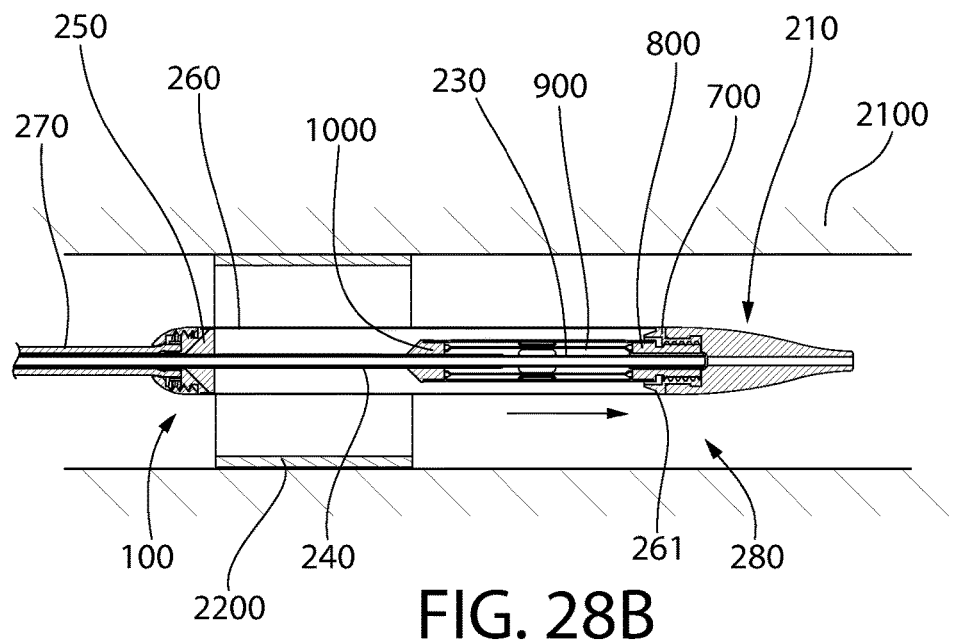

Referring to FIGS. 28A and 28B, next the surgeon rotates the outer handle 1800 clockwise relative to the handle threaded insert 1300, which causes the outer sheath 260 to move distally. The surgeon continues to rotate the outer handle 1800 clockwise until the expandable wall 900 is once again fully housed within the outer sheath 260 and the distal end 261 of the outer sheath 260 contacts the insert 700. At this point, the replacement aortic valve 2200 surrounds the outer sheath 260. Of course, in other embodiments the catheter 100 may be withdrawn from (i.e. slid through/past) the deployed TAV 2200 prior to re-sheathing the expandable wall 900 within the outer sheath 260. In such embodiments, the expandable wall 900 may be re-sheathed in the descending aorta. Thus, in some embodiments this re-sheathing step may take place after the step shown in FIGS. 29A and 29B described directly below.

Figure 29A:
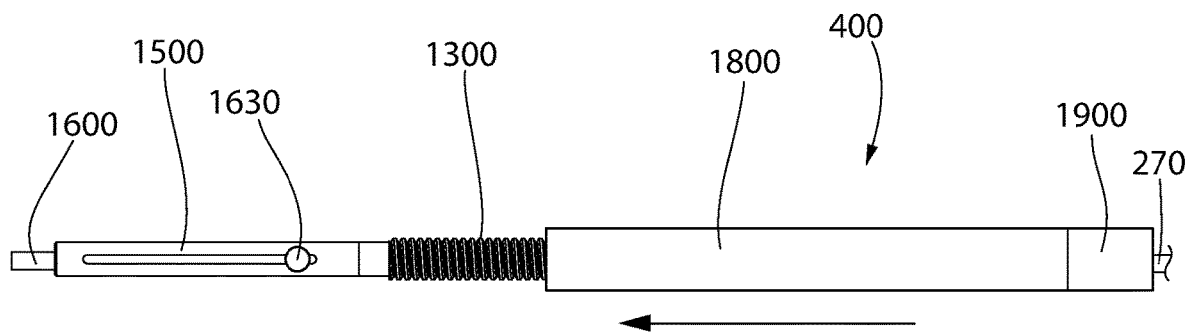
Figure 29B:
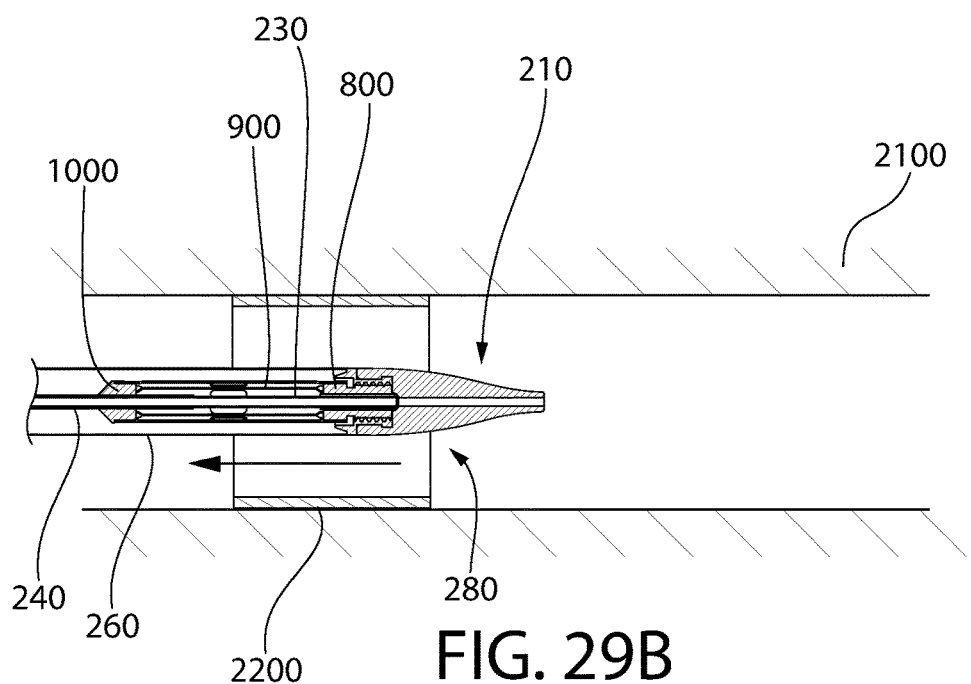

Finally, referring to FIGS. 29A and 29B, the surgeon withdraws the transfemoral catheter 100 from the patient 2100. During this step, the distal placement assembly 280 passes through an opening in the TAV 2200 and moves proximally until the entirety of the transfemoral catheter 100 is no longer located within the patient.

Various exemplary embodiments of the first tube 230 are contemplated. In one embodiment, the first tube 230 may be a braided tube for its entire length from the distal end 231 to the proximal end 232. In another exemplary embodiment, the first tube 230 may comprise a rigid metal tube at the distal end portion 231 where disposed within the expandable wall 900 and a braided tube proximally thereto. In yet another embodiment, the first tube 230 may be formed from nitinol as described herein.

Various exemplary embodiments of the second tube 240 is contemplated. In one embodiment, the second tube 240 may be a braided tube for its entire length from the distal end 241 to the proximal end 243. In another exemplary embodiment, the second tube 240 may comprise a rigid metal tube from the first distal end portion 241 through the second distal end portion 242, a braided tube within the second tubing assembly section 550, and a rigid metal tube where disposed with the handle section 400. Furthermore, the second tube 240 may be a laser cut hypotube in other embodiments as described herein.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

The invention claimed is:

1. A catheter comprising:
   an expandable wall assembly comprising a distal end and a proximal end;
   a first tube operably coupled to the distal end of the expandable wall assembly;
   a second tube operably coupled to the proximal end of the expandable wall assembly, at least a portion of the first tube being disposed within at least a portion of the second tube;
   a pusher attached to the second tube, the pusher spaced from the expandable wall assembly by a distance sized to accommodate a replacement aortic valve;
   an outer sheath having a lumen;
   wherein the outer sheath is movable between: (1) a first position wherein an expandable wall of the expandable wall assembly is located within the lumen of the outer sheath; and (2) a second position wherein the expandable wall of the expandable wall assembly is not located within the lumen of the outer sheath; and
   wherein axial translation of the first tube relative to the second tube while the outer sheath is in the second position alters the expandable wall of the expandable wall assembly between: (1) a first state in which the proximal and distal ends of the expandable wall assembly are separated by a first distance; and (2) a second state in which the proximal and distal ends of the expandable wall assembly are separated by a second distance, the first distance being greater than the second distance.

2. The catheter according to claim 1 further comprising a handle assembly, wherein a proximal end of the first tube and a proximal end of the second tube are secured to the handle assembly.

3. The catheter according to claim 2 wherein the handle assembly is configured to provide for the axial translation of the first tube relative to the second tube.

4. The catheter according to claim 1 wherein in the first state the expandable wall has a constant diameter and in the second state a portion of the expandable wall expands radially and the expandable wall has a non-constant diameter.

5. The catheter according to claim 3 wherein the handle assembly comprises a proximal slider that is housed within a proximal slider housing, the proximal end of the first tube being coupled to the proximal slider, and wherein moving the proximal slider axially in a proximal direction alters the expandable wall from the first state to the second state.

6. The catheter according to claim 2, wherein the handle assembly further comprises a distal slider assembly.

7. The catheter according to claim 6 further comprising a braided shaft comprising a distal end and a proximal end, the distal end of the braided shaft operably coupled to a proximal end of the outer sheath and the proximal end of the braided shaft operably coupled to the distal slider assembly.

8. The catheter according to claim 1 further comprising:
   the outer sheath comprising a distal end and a proximal end; and
   a connector comprising an interior lumen, a distal end, and a proximal end, the proximal end of the outer sheath connected to the interior lumen of the connector.

9. The catheter according to claim 1 further comprising a distal tip assembly coupled to the distal end of the expandable wall assembly.

10. A catheter comprising:
    an expandable wall assembly comprising a distal end and a proximal end;
    a first tube comprising a proximal end and a distal end, the first tube being coupled to the distal end of the expandable wall assembly so that axial movement of the distal end of the first tube towards the proximal end of the expandable wall assembly causes the distal end of the expandable wall assembly to move towards the proximal end of the expandable wall assembly;
    a second tube coupled to the proximal end of the expandable wall assembly;
    a pusher attached to the second tube in an axially spaced apart manner from the expandable wall assembly;
    a replacement aortic valve disposed around the second tube between the expandable wall assembly and the pusher;
    an outer sheath defining a lumen, at least a portion of the expandable wall assembly, the pusher, the replacement aortic valve, the first tube, and the second tube located within the lumen of the outer sheath;
    wherein the outer sheath is slidable relative to the expandable wall assembly, the pusher, the replacement aortic valve, the first tube, and the second tube.

11. The catheter according to claim 10 further comprising a handle assembly, wherein the proximal end of the first tube and a proximal end of the second tube are secured to the handle assembly.

12. The catheter according to claim 11 wherein the handle assembly is configured to provide for axial translation of the first tube relative to the second tube to provide for radially expanding and collapsing an expandable wall of the expandable wall assembly.

13. The catheter according to claim 11 wherein the handle assembly is configured to provide for axial translation of the outer sheath between: (1) a first position wherein the expandable wall assembly and the replacement aortic valve are located within the lumen of the outer sheath; and (2) a second position wherein the expandable wall assembly and the replacement aortic valve are not located within the lumen of the outer sheath.

14. The catheter according to claim 11 wherein the handle assembly comprises:
    a handle comprising a distal end and a proximal end;
    a threaded handle insert comprising a distal end and a proximal end;
    a proximal slider assembly comprising a distal end and a proximal end, the distal end of the proximal slider assembly secured to the proximal end of the threaded handle insert;
    the proximal slider assembly comprising a proximal slider housing and a proximal slider slidably disposed within the proximal slider housing;
    wherein the proximal end of the first tube is secured within the proximal slider; and
    wherein the proximal end of the second tube is axially secured between the proximal slider assembly and the threaded handle insert.

15. The catheter according to claim 11 wherein the handle assembly further comprises a distal slider assembly, and further comprising a braided shaft comprising a distal end and a proximal end, the distal end of the braided shaft operably coupled to a proximal end of the outer sheath and the proximal end of the braided shaft operably coupled to the distal slider assembly.

16. The catheter according to claim 10 further comprising:
the outer sheath comprising a distal end and a proximal end; and
a connector comprising an interior lumen, a distal end, and a proximal end, the proximal end of the outer sheath connected to the interior lumen of the connector.

17. The catheter according to claim 10 further comprising a distal tip coupled to the distal end of the expandable wall assembly, wherein no portion of the first tube protrudes from a distal end of the distal tip.

* * * * *